US010183183B2

(12) United States Patent
Burdette

(10) Patent No.: US 10,183,183 B2
(45) Date of Patent: Jan. 22, 2019

(54) ACOUSTIC APPLICATORS FOR CONTROLLED THERMAL MODIFICATION OF TISSUE

(75) Inventor: Everette C. Burdette, Champaign, IL (US)

(73) Assignee: ACOUSTIC MEDSYSTEMS, INC., Champaign, IL (US)

( * ) Notice: Subject to any disclaimer, the term of this patent is extended or adjusted under 35 U.S.C. 154(b) by 670 days.

(21) Appl. No.: 11/744,773

(22) Filed: May 4, 2007

(65) Prior Publication Data

US 2008/0255478 A1 Oct. 16, 2008

Related U.S. Application Data

(63) Continuation-in-part of application No. 11/787,096, filed on Apr. 13, 2007, now abandoned.

(51) Int. Cl.
*A61N 7/02* (2006.01)
*A61B 17/00* (2006.01)
*A61N 7/00* (2006.01)

(52) U.S. Cl.
CPC ...... *A61N 7/02* (2013.01); *A61B 2017/00761* (2013.01); *A61N 2007/0008* (2013.01); *A61N 2007/0065* (2013.01); *A61N 2007/0078* (2013.01)

(58) Field of Classification Search
CPC .................................... A61N 7/02; A61N 7/00
USPC ............................................................ 601/3
See application file for complete search history.

(56) References Cited

U.S. PATENT DOCUMENTS

| 4,326,529 | A | | 4/1982 | Doss et al. |
| 4,976,709 | A | | 12/1990 | Sand |
| 5,057,104 | A | | 10/1991 | Chess |
| 5,143,063 | A | | 9/1992 | Fellner |
| 5,391,197 | A | | 2/1995 | Burdette et al. |
| 5,456,259 | A | | 10/1995 | Barlow et al. |
| 5,471,988 | A | | 12/1995 | Fujio et al. |
| 5,522,869 | A | | 6/1996 | Burdette et al. |
| 5,533,401 | A | * | 7/1996 | Gilmore ............. G01N 29/0609 73/620 |
| 5,549,638 | A | | 8/1996 | Burdette |
| 5,620,479 | A | | 4/1997 | Diederich |
| 5,810,801 | A | | 9/1998 | Anderson et al. |
| 5,849,029 | A | | 12/1998 | Eckhouse et al. |
| 5,964,749 | A | | 10/1999 | Eckhouse et al. |
| 6,049,159 | A | | 4/2000 | Barthe et al. |

(Continued)

FOREIGN PATENT DOCUMENTS

WO  WO 2014028770  2/2014

OTHER PUBLICATIONS

Prionas et al., "Temperature Distributions Induced in Pig Tissues by a Water-Cooled Disk Electrode rf System", *Med. Phys.* 11(1), Jan./Feb. 1984, pp. 22-25, Am. Assoc. Phys. Med.

(Continued)

*Primary Examiner* — Hien Nguyen
(74) *Attorney, Agent, or Firm* — Foley & Lardner LLP

(57) ABSTRACT

An apparatus and method for modifying collagen containing dermal tissue. The apparatus includes a source of ultrasound energy comprised of a plurality of curvilinear ultrasound transducers shaped to direct ultrasound energy to selected skin depths. The transducers have variable curvature, drive frequency, power level and geometries to effect precise control of collagen modification.

21 Claims, 23 Drawing Sheets

(56) References Cited

U.S. PATENT DOCUMENTS

| | | |
|---|---|---|
| 6,050,943 A | 4/2000 | Slayton et al. |
| 6,113,559 A | 9/2000 | Klopotek |
| 6,254,553 B1 | 7/2001 | Lidgren et al. |
| 6,258,086 B1 | 7/2001 | Ashley et al. |
| 6,325,769 B1 | 12/2001 | Klopotek |
| 6,350,262 B1 | 2/2002 | Ashley |
| 6,350,276 B1 | 2/2002 | Knowlton |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,394,956 B1 | 5/2002 | Chandrasekaran et al. |
| 6,405,090 B1 | 6/2002 | Knowlton |
| 6,413,255 B1 | 7/2002 | Stern |
| 6,425,912 B1 | 7/2002 | Knowlton |
| 6,430,446 B1 | 8/2002 | Knowlton |
| 6,438,424 B1 | 8/2002 | Knowlton |
| 6,461,378 B1 | 10/2002 | Knowlton |
| 6,470,216 B1 | 10/2002 | Knowlton |
| 6,575,969 B1 | 6/2003 | Rittman et al. |
| 6,595,934 B1 | 7/2003 | Hissong et al. |
| 6,626,902 B1 | 9/2003 | Kucharczyk et al. |
| 6,673,063 B2 | 1/2004 | Brett |
| 6,726,684 B1 | 4/2004 | Woloszko et al. |
| 6,929,640 B1 | 8/2005 | Underwood et al. |
| 6,980,862 B2 | 12/2005 | Fredricks et al. |
| 7,270,658 B2 | 9/2007 | Woloszko et al. |
| 7,331,956 B2 | 2/2008 | Hovda et al. |
| 7,462,178 B2 | 12/2008 | Woloszko et al. |
| 7,473,224 B2 | 1/2009 | Makin |
| 7,806,892 B2 | 10/2010 | Makin et al. |
| 8,292,815 B2 | 10/2012 | Burdette et al. |
| 9,119,954 B2 | 9/2015 | Burdette et al. |
| 2001/0003791 A1* | 6/2001 | Burbank et al. .............. 600/431 |
| 2001/0031922 A1* | 10/2001 | Weng et al. .................. 600/439 |
| 2002/0016546 A1 | 2/2002 | Cerofolini |
| 2002/0035361 A1* | 3/2002 | Houser et al. ................. 606/15 |
| 2002/0095144 A1 | 7/2002 | Carl |
| 2002/0151940 A1 | 10/2002 | Bar-Cohen et al. |
| 2003/0013960 A1 | 1/2003 | Makin et al. |
| 2003/0014093 A1 | 1/2003 | Makin |
| 2003/0032898 A1 | 2/2003 | Makin et al. |
| 2003/0069569 A1 | 4/2003 | Burdette et al. |
| 2003/0130598 A1 | 7/2003 | Manning et al. |
| 2003/0163067 A1 | 8/2003 | Lidgren |
| 2003/0216721 A1 | 11/2003 | Diederich et al. |
| 2005/0015024 A1 | 1/2005 | Babaev |
| 2005/0036976 A1* | 2/2005 | Rubin et al. .................... 424/74 |
| 2005/0090816 A1 | 4/2005 | McClurken et al. |
| 2005/0228318 A1 | 10/2005 | Iger |
| 2005/0261584 A1 | 11/2005 | Eshel et al. |
| 2006/0074314 A1* | 4/2006 | Slayton .................... A61B 8/14 600/439 |
| 2006/0074355 A1* | 4/2006 | Slayton et al. .................... 601/2 |
| 2006/0241436 A1* | 10/2006 | Sunnanvader ................ 600/438 |
| 2007/0016062 A1 | 1/2007 | Park et al. |
| 2007/0203555 A1 | 8/2007 | Williaims |
| 2008/0004614 A1 | 1/2008 | Burdette et al. |
| 2008/0125674 A1 | 5/2008 | Bilecen et al. |
| 2009/0018446 A1 | 1/2009 | Medan et al. |
| 2009/0292199 A1 | 11/2009 | Bielewicz et al. |
| 2010/0312096 A1 | 12/2010 | Guttman et al. |

OTHER PUBLICATIONS

Diederich et al., "An Improved Bolus Configuration for Commercial Multielement Ultrasound and Microwave Hyperthermia Systems", *Med. Phys.* 21(9), Sep. 1994, pp. 1401-1403, Am. Assoc. Phys. Med.

Diederich et al., "Transurethral Ultrasound Applicators with Directional Heating Patterns for Prostate Thermal Therapy: In Vivo Evaluation Using Magnetic Resonance Thermometry", *Med. Phys.* 31(2), Feb. 2004, pp. 1-9, Am. Assoc. Phys. Med.

European Communication dated Jan. 23, 2013 for EP Application No. 08 745 765.1, 5 pages.

Chopra et al., MRI-compatible transurethral ultrasound system for the treatment of localized prostate cancer using rotational control, Medical Physics, vol. 35. No. 4, Apr. 2008, pp. 1346-1357.

Diederich et al, Catheter-Based Ultrasound Devices and MR Thermal Monitoring, for Conformal Prostate Thermal Therapy, 30th Annual International IEEE EMBS Conference Vancouver, British Columbia, Canada, Aug. 20-24, 2008, pp. 3664-3668.

Prakash, et al., Patient Specific Optimization-Based Treatment Planning for Catheter-Based Ultrasound Hyperthermia and Thermal Ablation, Proceedings of SPIE, vol. 7181 71819E, 2009, 11 pages.

Ross et al., Highly directional transurethral ultrasound applicators with rotational control for MRI-guided prostatic thermal therapy, Physics in Medicine and Biology, vol. 49, No. 2. pp. 189-204, Jan. 21, 2004.

Office Action in U.S. Appl. No. 14/421,902, dated Jul. 28, 2017, 11 pages.

Office Action in U.S. Appl. No. 14/841,586, dated Aug. 4, 2017, 12 pages.

Diederich, C.J., et al., "Ultrasound Technology for Hyperthermia", Ultrasound in Med. & Biol., Mar. 26, 1999, 25(6):871-887.

El-Desouki, M. M., et al., "Driving Circuitry for Focused Ultrasound Noninvasive Surgery and Drug Delivery Applications", Sensors, Jan. 7, 2011, 11:539-556.

Hynynen, K., et al., "Image-guided ultrasound phased arrays are a disruptive technology for non-invasive therapy", Phys. Med. Biol., Aug. 5, 2016, 61:R206-R248, and corrigendum, 2018.

Office Action in U.S. Appl. No. 14/421,902, dated Jul. 26, 2018, 20 pages.

\* cited by examiner

*FIG. 1*  *Prior Art*
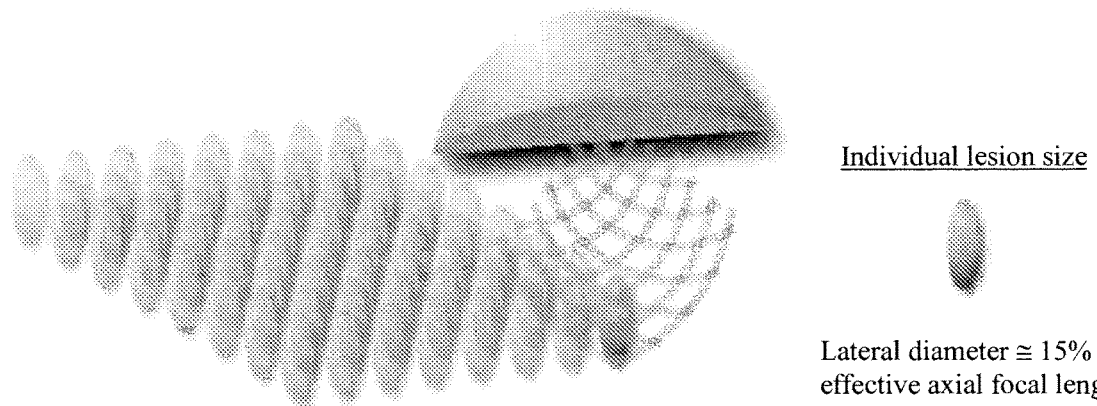
Individual lesion size
Lateral diameter ≅ 15% of effective axial focal length
*FIG. 2*  *Prior Art*
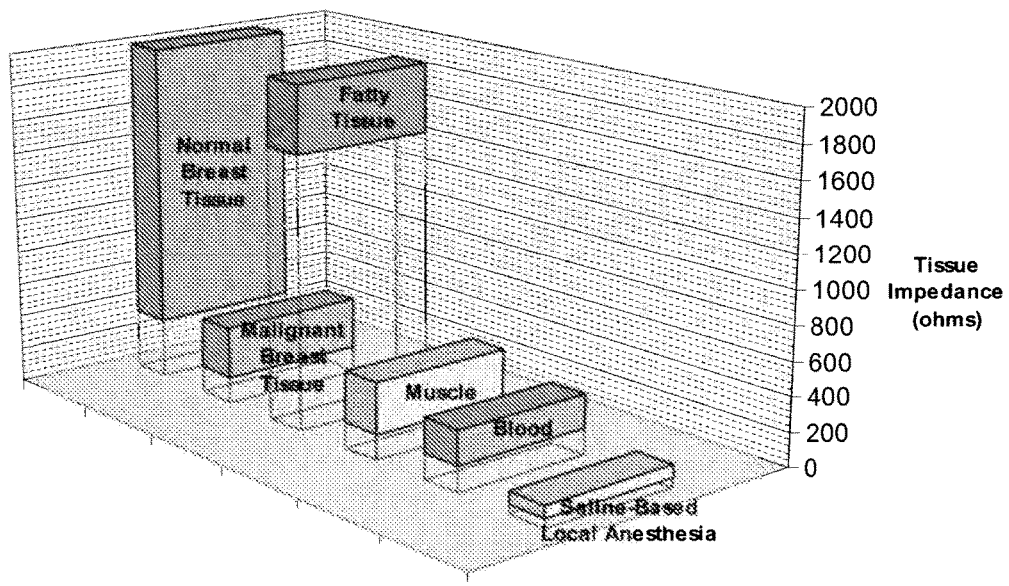

FIG. 3 *Prior Art*
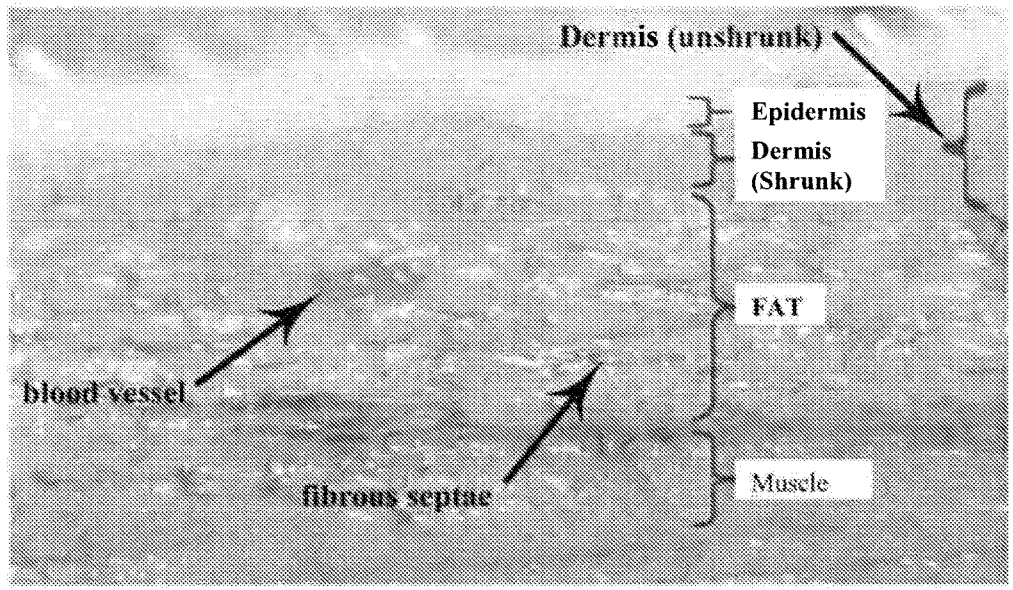
FIG. 4 *Prior Art*
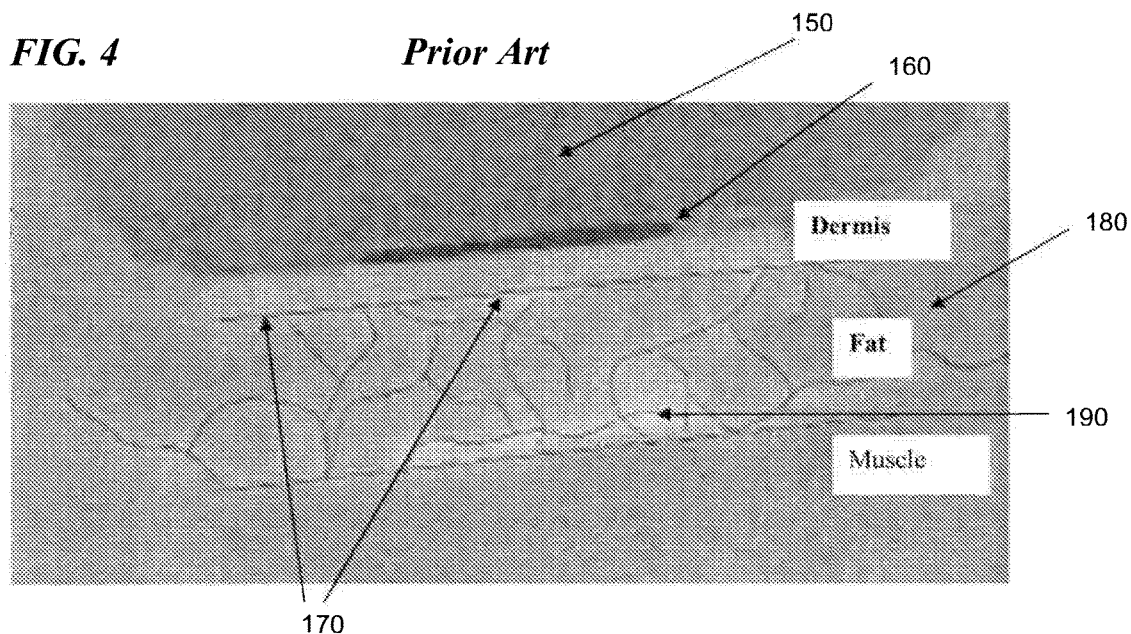

150

190

FIG. 7                                                      *Prior Art*
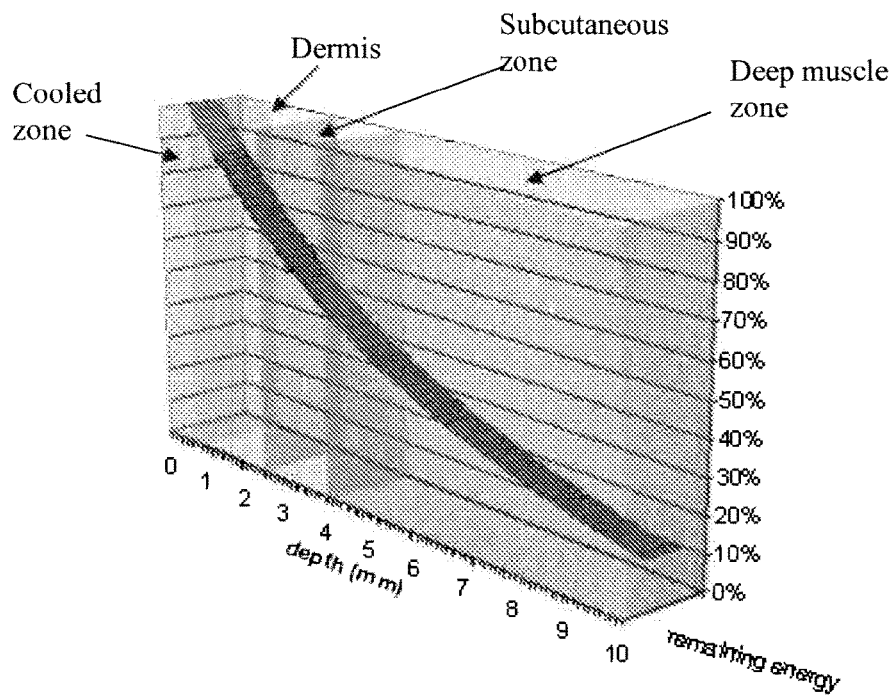
FIG. 8                                                      *Prior Art*
Continuous contact cooling
Infrared Light Source
Handpiece End View Top View Side View Sensor Locations Setup 2 and 3

End View

Top View

Side View

Sample 1, Heating pattern in pork skin from 4.5 seconds of acoustic power

Sample 3, Heating pattern in porcine skin from 30 seconds of 2.5 Watts acoustic power

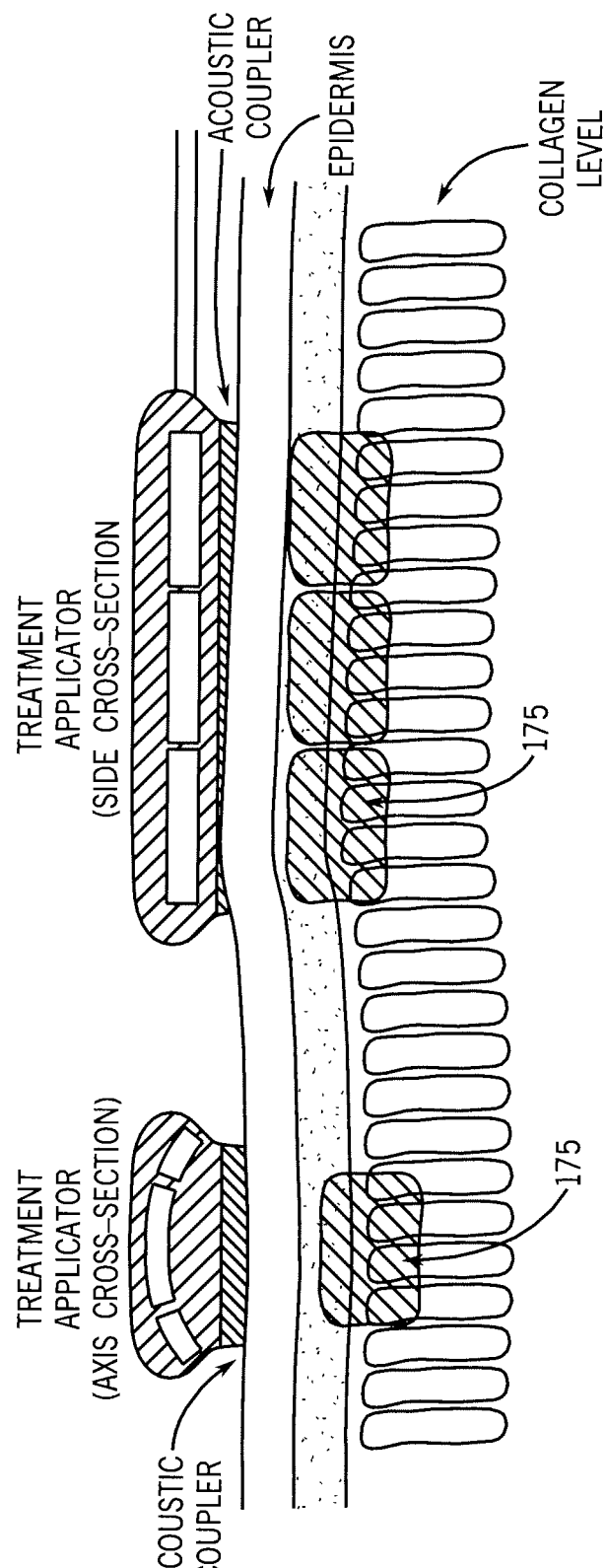

ACOUSTIC APPLICATORS FOR CONTROLLED THERMAL MODIFICATION OF TISSUE

CROSS-REFERENCE TO RELATED PATENT APPLICATIONS

This application is a continuation-in-part of U.S. patent application Ser. No. 11/787,096 filed Apr. 13, 2007, and which is incorporated herein by reference in its entirety.

FIELD OF THE INVENTION

This invention relates to apparatus and methods using acoustic energy for controlled induction of changes in the collagen content and/or structures in tissue with an emphasis on skin tissue treatment for tightening and rejuvenating the skin, reducing wrinkles, and also for treating acne.

BACKGROUND OF THE INVENTION

As more members of the "baby boomer" generation age, the number of surgical procedures to maintain a youthful appearance continues to increase. Of these cosmetic procedures, a significant increase has been in the area of non-invasive aesthetic applications. Many laser based systems are on the market with FDA clearance to non-ablatively treat wrinkles and rejuvenate skin texture. Lasers treat the skin and underlying subcutaneous tissues by depositing light energy to heat the tissues. The depth of treatment, however, is limited by the laser wavelength.

An alternative heating method is radiofrequency (RF) heating which provides variable heat penetration. RF energy can be delivered to skin tissues for aesthetic and therapeutic effect using either monopolar or bipolar electrode-coupled induction techniques. These systems require the use of active cooling at the interface between the skin surface and the electrodes to prevent localized burning.

The clinical opportunity in the field of skin tightening/wrinkle removal is therefore very significant and is an accepted treatment. However, that established market is being addressed to varying degrees by technologies which, though they are state-of-the-art today, leave the physician and customer base less than satisfied. These procedures for example require aggressive skin cooling in conjunction with laser/light therapies to provide treatment from just below the epidermis to approximately 0.5-1.0 mm below the skin surface, as well as the various RF induction methods, with low reproducibility of clinical results/outcomes due to inherent limitations in the physics of the approach.

It has long been known that damaging collagen will cause shrinkage and neocollagenesis (rejuvenation). It has been shown that the physiology will allow excellent clinical results that will allow physicians and device companies to serve patients profitably—but they have also proven that those results are often inconsistent. In some cases the clinical outcome is dramatic, in others it is imperceptible, and in still others the end result can be worse than the initial condition (significant burns, overshrinkage and loss of skin form). The cause of these inconsistent clinical results is related to the types of technology applications that apply the thermal energy with these devices—which are, themselves, inconsistent. The goal of the treatment is to heat the underlying tissue (dermis), and some of the deeper tissue, at temperatures ranging from 55° C. to 70° C. for a short period of time while leaving the surface (epidermis) and underlying tissue unaffected. Existing technologies are not able to accurately control where they apply the therapeutic treatment, depth of penetration, or how much therapeutic energy is absorbed by the target region.

There are three primary approaches being pursued by conventional systems using energy to treat skin and subcutaneous fat for aesthetics purposes, (1) disruption of the fat cells through agitation and cavitation to affect liposuction (may be performed invasively or noninvasively), (2) affecting thermal injury to the skin surface (epidermis) to stimulate neocollagenesis (the forming of new tissue) to smooth the texture of the skin, and (3) affecting thermal elevation of the tissue underlying the epidermis to affect removal of deeper wrinkles and tighten sagging skin.

Variations in High Intensity Ultrasound technologies—cellular disruption vs acoustic stimulation to heat tissue. To those who are not experts in the field it may appear that High Intensity Focused Ultrasound (HIFU) is the primary term used to describe the application of acoustic energy for thermal therapy applications and that there are several participants in this field. Actually, HIFU is specific to a particular method of delivery of acoustic energy, and does not encompass several other methods to use ultrasound for treatment.

There are five conventional variations to therapeutic applications of ultrasound:
(1) Low intensity, low frequency stimulation of bone tissue to encourage bone healing or to increase membrane permeability for the purpose of increased membrane transport of chemical agents.
(2) High intensity, low frequency application to affect cellular disruption. The primary applications for this family of devices are for disruption of fat cells in liposuction or disruption of thromboses in vascular structures.
(3) Low intensity, high frequency application to affect therapeutic heating for muscle soreness. A variety of products in the field of sports medicine have been employed for years.
(4) High intensity, high frequency application to produce molecular agitation and directly interact with the high frequency mechanical properties of the tissue to produce localized heating within a desired therapeutic zone:
 a. The delivery approaches vary, and the use of hemispherical focused transducers is incorporated in the prior art products, and this is the typical HIFU. These include products for "spot" ablation of cancerous tissue and Benign Prostate Hyperplasia (BPH), creating cardiac lesions to treat atrial fibrulation (E), and tissue dissection/tissue welding.
 b. Technology that uses tubular and curvilinear soft-focus and line focus transducer technology in both singular and array structures to create a customized shaped volume region of therapy. This can be achieved through explicit transducer design on an a priori basis and using multiple element designs integrated to permit dynamic adjustment of the therapeutic size and shape, dependent upon the specific tissue treated. Thus, volumetric heating of customized shapes and sizes can be achieved. For mid-size and larger regions, this permits treatment times that are much shorter than achieveable with "step focused" systems. Further, the control of the customized shape and treatment volume is exquisite, permitting an exact lesion size or treatment region to be created.

(5) Acoustic Shock Wave Lithotripsy (ASWL) for disruption of calcium deposits such as kidney stones and bone spurs.

Regarding methodology 4(a) above, (HIFU) approaches use hemispherical transducers to create focal points of energy (see FIG. 1). This approach works well when the desired result is to create a "cigar-shaped" lesion as the approach would produce a very high intensity energy density in the lateral cross section at the focal depth with a focal length of approximately eight times the lateral focal cross section which is centered at the focal depth. An example would be an external or intracavitary transducer focused at a depth of 3 cm that has a focal zone with a 1 mm cross section and a focal length of 8 to 10 mm. Depending upon the frequency, focal length, focal gain and input power, it is possible to create extremely high power densities at the center of each focal zone. Exquisite control of such energy using real-time, spatially-registered imaging is a requirement to deliver treatment that doesn't leave "gaps" laterally and doesn't seriously injure nearby normal tissues.

Creating a volumetric lesion with standard HIFU approaches would require the creation of multiple small lesions to cover the desired lateral cross section. As an example, a 1 cm$^2$ square lateral region would require approximately eight half-power-width overlapping zones in both lateral directions, producing a 1 cm×1 cm lateral by 1 cm depth zone of temperature elevation. This would require the creation of 64 separate focal zones. Treatment using such an approach would be slow (approximately 60 seconds for a 1 cm region) and non-uniform in treatment.

When affecting a thermal increase in deeper tissue while leaving the tissue adjacent to the applicator probe (i.e. the skin) relatively unaffected, focused ultrasound technology is intrinsically superior to radiofrequency methods for two reasons:

(1) The electrical properties of various tissue types (epidermis, dermis, subcutaneous fat, fibrous septae, and subcutaneous muscle) vary much more than the acoustical properties of those tissue structures. This is because the electrical properties are dominated by water and electrolyte (salt) content, whereas the acoustic properties are predominately dependent on density differences. The result in this wider variation is that the tissue resistivity. Therefore, RF energy is not uniformly absorbed by the tissue below the application probe.

RF power is not propagated through the tissue. RF is resistive in absorption, i.e. like connecting a network of resistors in a series-parallel combination across a big battery and heating the resistors along the available current pathways. Any propagation of the resultant heat is due to the thermal conductivity of the tissue. Any propagation of the resultant heat to neaby tissue is due to the thermal conductivity of the respective tissue. Small variations in tissue composition and variations in blood perfusion, therefore, can dramatically affect the electrical properties of the tissue and the energy absorption profile with RF treatment (and thus the treatment efficacy) of the underlying tissue. This phenomenon will be discussed in greater detail below.

With a more consistent energy absorption profile from energy that is propagated through the tissue (with ultrasound) the energy absorption (and treatment efficacy) are more uniform and predictable.

(2) Because RF is a resistive heating phenomenon, dependent on the current density in the tissue, most of the RF effect occurs directly at the electrode/skin interface.

Between 50% and 90% of the current (thus resistive heating) occurs in the 750 um of epidermis (a region which must be cooled to prevent skin burns). This means that most of the energy is dissipated and unproductive. Not only is this inefficient, but if there is a variation in tissue characteristics in the region within and below the cooled zone, dramatic changes in energy disposition to the region outside of the cooled zone could occur. Paths of high tissue conductivity next to those that are more resistive produce widely varying RF absorption patterns, often dramatically affecting resultant heating patterns.

To illustrate this point further—if 75% of the energy is supposed to be dissipated in the cooling process, then only 25% of the energy is delivered to the region to be treated. If the low resistance components (saline from sweat, etc.) are twice as prevalent in the 750 um surface zone, then more energy (than expected) will be delivered to the deeper zone. Since there is no consistent means of monitoring where this energy is deployed, there could be rapid heating and tissue overtreatment in some areas and undertreatment in others within this region.

To illustrate the first point in more detail, the graph in FIG. 2 depicts the known electrical properties of several types of tissue. For example, fatty tissue has impedances ranging from 1,600 ohms to 2,000 ohms, while blood has a resistance of 150 ohms to 200 ohms. Since the cross sectional area of a small vessel could be 0.5 mm, such a structure in a 1.5 cm$^2$ treatment zone represents only 0.5% of the area through which current would travel, but the current density would be ten times that of the surrounding tissue. Therefore, one structure, which is only 0.5% of the current-carrying media, would carry 3.5% of the current to the underlying tissue.

In conventional RF systems, such as described in: "Selective Fibrous Septae Heating". An additional mechanism for Capacitively Coupled Monopolar Radiofrequency", (Karl Pope, Mitch Levenson, E. Vic Ross, MD), the subcutaneous tissue is described as being a network of blood vessels and collagenous structures which connect the dermis to the underlying muscle (the fibrous septae). This anatomy is depicted in FIG. 3. It is asserted that for such RF systems the fibrous septae have significantly lower electrical impedance properties than the surrounding fatty tissue. An infrared image obtained during treatment (FIG. 4 from the prior art cited above) shows non-uniform heating of the underlying tissue. The probe 150 is visible and a cooled region 160 is directly below. The heated regions 170 appear non-uniform within the normal tissue 180. It should be emphasized that these are untouched replications from the literature article, and the lines (drawn by the authors of the paper) are estimations of the location of fibrous septae. The authors' intention was to depict deeper heating and contraction of the fibrous septae.

This image from the prior art literature provides significant clues of the shortcomings of the RF procedure. In FIG. 4 most of the heating appears to be at the fat/muscle interface—about 4 mm to 6 mm below the surface of the probe 150. This would make sense if, as the authors claim, the surface is being cooled and the excess current is being shunted through the surface tissue to the underlying muscle. The intense heating at this interface can explain the fat necrosis which has occurred in several RF heating cases known in the art. In fact, there is a zone in the fat/muscle interface depicted in the tissue cross-section, which appears to show some fat necrosis.

Note also that the heating under the probe 150 is not uniform. There are portions of intense heating in the epidermis (see the bright yellow region on the right, behind the label "Dermis"), while the cooling effect seems to occur under only half of the probe 150. The 2 mm of dermal tissue contains regions of the heated region 170 and the unheated normal tissue 180.

Another fact that the reader should note is that, even in the image depicting a prior art "shallow probe" (See FIG. 5), that there is very little cooling in the epidermal region immediately adjacent to the probe 150 and there is a zone of significant heating at the fat/muscle interface 190 some 4 mm to 6 mm deep.

The tissue cross-sectional photograph from the prior art presents some inconsistencies in the theory. FIG. 3 shows a dense network of fibrous septae—but the infrared (IR) photograph in FIG. 4 shows only a few shunting paths. Either the shunting is occurring along different paths (perhaps blood vessels), or some fibrous septae are more electrically conductive than others. Further, the tissue cross-section photograph shows no shrinkage in the fibrous septae-rich subcutaneous zone. There is significant shrinkage in the dermal layer—as one would expect—but there is none in the underlying zone. The thermal shunting in the underlying zone seems only to contribute to fat necrosis.

These images, indicate that uniform heating with RF is not easily achieved (if it is achievable at all). The acoustic properties of tissue are much more uniform, with the acoustic absorption between brain, kidney, liver, and muscle at a given frequency varying by 15% or less (for purposes of showing the state of the art, see Table 4.19, page 116 in Duck, F A, *Physical Properties of Tissue*, Academic Press, 1990. Tissue heating is a function of the acoustic velocity and attenuation through the specific tissue type. In general, absorption is directly related to the tissue density. Unlike the case for RF, acoustic energy actually is transmitted through soft tissues and it loses energy to heat conversion as it propagates. By selecting the frequency and focusing parameters judiciously, a large portion of the propagated energy is converted to heat directly in the desired region. The high degree of directivity is attained because at higher frequencies (in the MHz range) the wavelengths are short and can be directed and/or focused, just like light. However, the penetration is significantly greater. Insert Fat Necrosis Comment w/acoustic absorption.

Another conventional device employs a bipolar electrosurgical approach. The theory behind this approach is that the current would pass from one electrode to the other, staying in the underlying tissue. Unlike the RF electrodes described for the RF system, however, which are planar, the electrodes may be considered to approach two short linear sources. As such, the current density (and associated power) fall off as a factor of $1/R^3$ (as opposed to $1/R^2$ or $1/R$ for the planar approach. Most of the current flows along the surface of the tissue. It is virtually impossible to create any heating at depth.

Depending on whether the dissipation mechanism falls off at $1/R^2$ or $1/R$, the monopolar approach results in between 50% and 90% of the energy is applied to the 750 um of epidermal tissue which is cooled to prevent burning (see FIG. 6A). The bipolar system of FIG. 6B, with a dissipation mechanism that falls off at $1/R3$, more than 99% of the energy is applied to that 750 um cooled zone. This design feature leaves very little energy available for tissue treatment. Only 10% to 50% of the thermal effect occurs in the zone outside of the cooled epidermis (blue zone in graph) with the monopolar approach. With the bipolar approach of FIG. 6B only 1% of the thermal effect occurs in the zone outside the cooled epidermis. A significant quantity of thermal effect occurs beyond the therapeutic zone with the monopolar approach.

The above described electrosurgical methods for deep skin heating are not uniform and/or not predictable, or produce so little thermal action that they are ineffective. The bipolar linear electrodes produce very little effect. The monopolar planar electrodes allow current to shunt through low impedance structures to produce non-uniform heating in the dermis with a concentration at the fat/muscle interface, which could contribute to fat necrosis.

In light based treatment approaches, the theory behind light-based deep tissue heating requires applying a radiant energy source which dissipates as a function of depth while cooling the surface. The method of action is actually very different from the RF approach, but both have the result that the thermal effect is significantly greater at the probe/tissue interface (skin) than in deeper layers.

With light-based approaches, the molecular entities in the tissue (primarily water) absorb the photons from light-based energies and convert that energy (more-or-less) directly to heat, and that the light energy dissipates much less dramatically than RF. For instance, according to Franceschini, et al, ("Near-Infrared Absorption and Scattering Spectra of Tissues in Vivo") presented at the SPIE in 1999 (http://www.eotc.tufts.edu/Documents/Faculty/Franceschini/papers/spie99-mari.PDF), the absorption rate of infrared light in skin tissue is approximately 20%/cm.

A chart of this absorption profile is presented in FIG. 7. Note that, although a significant amount of applied energy is transmitted beyond the cooled zone (85%), only 20% is absorbed in the therapeutic zone of the dermis, another 20% is absorbed in the subcutaneous fat, and more than 40% is transmitted into the deeper muscle tissue. 15% of the light is absorbed in the cooled zone of the epidermis, 20% in the therapeutic zone of the dermis, 20% in the subcutaneous fat, and 45% in the deeper muscle tissue. Although the skin is spared damage by the cooling process, there is no means of controlling thermal injury to the subcutaneous fat and deeper muscle.

The light-absorbing characteristics of tissue are much more uniform than the electrical characteristics. Thus, light absorption is more gradual and doesn't exhibit the large unpredictabilities found with RF approaches. In Franceschini's paper referenced above, the absorptive characteristics of the three patients ranged from 10%/cm to 25%/cm (a factor of 2.5, while the difference between the electrical impedance of fat and blood could be a factor of 10). There are factors, however, such as the concentration of melanocytes (such as with certain ethnic groups, or variations after recent exposure to the sun) that also affect the absorption levels. Melanocytes act as "absorbers" that selectively absorb light energy, producing inhomogeneous energy absorption, depending upon the amount degree of their presence and uniformity. This can yield highly variable results in such instances. Although the skin is spared thermal injury by the cooling process, there is no means of controlling injury to the subcutaneous fat and deeper muscle.

In another conventional device shown in FIG. 8, infrared energy is applied to the underlying tissue. The prior art device transmits infrared light in the range of 1,100 nm to 1,800 nm. The contact head has a cooling mechanism to protect the skin from burning. There is no mechanism to protect the deeper subcutaneous fat and muscle from thermal injury.

In another light based system (not shown), a NdYAG laser is used and, which transmits in the 1,064 nm range. The device also incorporates epidermal cooling to spare skin damage. This type of devices operates on the principle of applying infrared energy to the underlying tissue. The device transmits infrared light in the range of 1,100 nm to 1,800 nm. The contact head has a cooling mechanism to protect the skin from burning.

Light-based energy sources can effectively heat the near dermal and subcutaneous layers to affect treatment. They transmit only a small portion of their energy in these regions, however, and they cannot control the energy applied to deeper subcutaneous fat and muscle. In order to avoid injuring these deeper structures, they must limit the amount of energy applied altogether. This, in turn, limits the amount of energy applied to the dermal zone and thus, the effectiveness of the treatment. Further, the presence of variable degrees of melanocytes can produce unpredictable variability in absorption.

OBJECTS OF THE INVENTION

It is therefore an object of the invention to provide an improved controlled and directive delivery of a thermal dose to a pre-selected tissue region in the body for the purpose of thermal therapy for collagen reformation and rejuvenation and/or for the treatment of disease.

It is a further object of the invention to provide an improved method and system to treat skin using ultrasound energy for aesthetic purposes and for causing changes in dermal and sub-dermal tissues resulting in skin tightening and rejuvenation.

It is yet a further object of the invention to provide an improved method and system to deliver ultrasound energy to tissue in a region beginning beneath the epidermis and extending through a depth zone "thickness" of from 2 mm to 10 mm.

It is still a further object of the invention to provide an improved method and system to be able to deliver the ultrasound therapeutic depth zone at different overall depths beginning at 1-2 mm beneath the skin surface to 4-10 mm depth, or begin as deep as about 60 mm to 80 mm beneath the skin surface and extend to as deep as 100 mm with a focal depth zone of from 5 mm to 20 mm.

It is another object of the invention to provide an improved method and system to create a therapeutic ultrasound thermal dose using ultrasound delivered by external means for transdermal cosmetic and therapeutic treatment of skin, subdermal adipose, and subdermal fibrous septae tissue structures not extending below the fat-muscle interface and use imaging of tissue property changes for monitoring of treatment.

It is a further object of the invention to provide an improved method and system to treat skin using ultrasound energy for aesthetic purposes and for causing changes in epidermal and near dermal tissue resulting in skin tightening and rejuvenation.

It is yet another object of the invention to provide an improved modular systems and to provide configurations that can treat lateral regions of different extent.

It is another object of the invention to provide improved methods and systems to treat different size zones of tissue for different sites on the human body.

It is still another object of the invention to provide an improved method and system to use the reflected ultrasound energy as a monitor of tissue density and structural changes during the delivery of thermal therapy.

It is another object of this invention to provide an improved method and system to use the measured tissue changes to correlate to tissue damage with changes in tissue structure and/or acoustic property changes as a result of treatment.

It is yet another object of the invention to provide an improved method and system to produce acoustic energy patterns which are used to treat diseases of skin and subcutaneous tissues including acne, psoriasis, and skin cancer.

SUMMARY OF THE INVENTION

In one embodiment, the instant system comprises small curvilinear ultrasound transducers positioned in the disposable portion of a therapy applicator, designed for direct contact at a treatment site (surface interface, minimally-invasive catheters and needles). High-power ultrasound energy is emitted from the applicator and absorbed locally in the target tissue, producing high temperatures (>55° oC.) that rapidly coagulate and thermally destroy the target volume within seconds. The power output and temperature is controlled and monitored with a portable PC-based generator/control module. The entire treatment can be performed as an outpatient procedure using no anesthesia (depending upon anatomical site treated—i.e. external vs internal), and the patient can return home the same day without complications or side effects.

There are significant advantages of high-frequency therapeutic ultrasound with the appropriate instant therapy transducer design herein described. These capabilities in the described combination of elements simply are not possible with other thermal therapy devices:

(1) 3-D control and directionality of the ultrasound energy delivery⇒the ability to treat a prescribed target volume and shape (2) ultrasound energy penetration into the target tissue⇒the ability to treat larger target volumes, as well as shorter treatment times (3) dynamic control of the amount and distribution of energy delivered⇒the ability to monitor tissue and to change the thermal target volume during the treatment process.

Ultimately, this superior control of ultrasound energy delivery can provide conformal therapy to a defined treatment margin, completely destroying the target volume while preserving the surrounding healthy tissue. The curvilinear transducers of the preferred embodiment are based upon a sub-cylindrical longitudinal sectioning of a cylindrical transducer or alternatively, a parabolic-shaped transducer. Other arcurate geometries can also be used to achieve specific desired therapeutic zone heating.

With regard to the zone of soft focus of acoustic energy, which may be affected by the instant ultrasound delivery device, that focus can be delivered by a single transducer, or a plurality of transducers aligned adjacent to each other. In the case of each transducer element, the exact size of the lateral pattern (size on skin surface) is determined by the transducer length along its long axis, its width (related to radius of curvature), frequency of operation, and desired zone of focus (depth and extent). Multiple transducer elements may be assembled to form an array. This permits larger areas to be covered with a single application. Further, these individual transducers may be located within the applicator to form an additional curvilinear region, permitting further concentration of energy in a narrower depth zone while having significant (2-4 cm) lateral coverage. With the single transducer, a pattern of thermal elevation may be created which is as long as the curvilinear transducer (we have experience up to 4 cm in length) and approximately 70% of the width of the transducer.

The present invention can thus be used to treat skin tissue for producing skin tightening, rejuvenation, and wrinkle reduction at any location on the body, including face, jowels, abdomen, thighs, and buttocks, and including subdermal regions considered too large or deep for existing light-based heating technologies. It is often difficult to treat at multiple depths and over various sized lateral regions with existing techniques. Only ultrasound technology allows both directional control and deep penetration of energy patterns. With this approach, various regions of differing size can be treated by targeting the acoustic energy to specific depth and lateral zones, thus reducing the treatment time and improving chances for effective, durable response. This method does not experience the variability in dose distribution and depth experienced with other induction modalities. This is directed controlled-dose thermal therapy at a prescribed depth range using acoustic applicators designed for energy delivery for specific depth and lateral regions.

The objects and the advantages of the invention are described hereinafter and preferred embodiments illustrated in the drawings described hereinbelow.

BRIEF DESCRIPTION OF THE DRAWINGS

FIG. 1 illustrates a prior art HIFU system;

FIG. 2 illustrates electrical characteristics of selected tissue type;

FIG. 3 illustrates anatomy of subcutaneous tissue;

FIG. 4 illustrates an infrared image of a prior art radiofrequency (RF) treatment;

FIG. 7 illustrates an absorption profile in a light based skin treatment system;

FIG. 8 illustrates a conventional infrared light treatment device;

FIG. 27A shows an end view of the placement of a curvilinear transducer array on the surface of the skin configured to produce a focus at the sub-dermal level; and FIG. 27B shows a side view of the transducer array within the handpiece and coupling through an acoustic coupler to the surface of the skin.

DETAILED DESCRIPTION OF PREFERRED EMBODIMENTS

In a preferred method and system of the invention, various configurations of single transducers 100 and cylindrical, partially cylindrical and planar ultrasound transducers arrays 130 are shown in FIGS. 9A-9D. These transducer varieties are configured and mounted to obtain specific directive patterns and efficient therapeutic energy output levels. These transducers 100 and arrays 130 are, for example, mounted within a hand held delivery/applicator device (not shown) designed for direct skin contact at a treatment site (surface interfaces—skin, minimally-invasive catheters and needles). High-power ultrasound energy is emitted from the transducers 100, 130 and absorbed locally in the targeted tissue, rapidly producing high temperatures (>55° C.) that either thermally treat or necrose the target volume within seconds. The power output and temperature is controlled and monitored with a portable PC-based ultrasound system 120 shown schematically in FIG. 10. The entire treatment can be performed as an outpatient procedure using no anesthesia (depending upon anatomical site treated—i.e. external vs internal), and the patient can return home the same day shortly following treatment without complications or side effects.

There are significant technical advantages of high-frequency therapeutic ultrasound with appropriate therapy transducer design configurations. These capabilities are inherent with high-frequency ultrasound implemented in the preferred embodiments described herein and include, for example:

(1) 3-D control and directionality of the ultrasound energy delivery⇒the ability to treat a prescribed target volume and shape
(2) ultrasound energy penetration into the target tissue⇒the ability to treat larger target volumes, as well as shorter treatment times than other approaches, including HIFU
(3) dynamic control of the amount and distribution of energy delivered⇒the ability to change the thermal target volume during the treatment process.
(4) uniformity in treatment (with respect to radiofrequency)⇒the ability to minimize the variation in thermal dose to the treated tissue resulting in reproducible clinical outcomes Ultimately, this superior control of ultrasound energy delivery can provide conformal therapy to a defined treatment margin.

Figure 5:
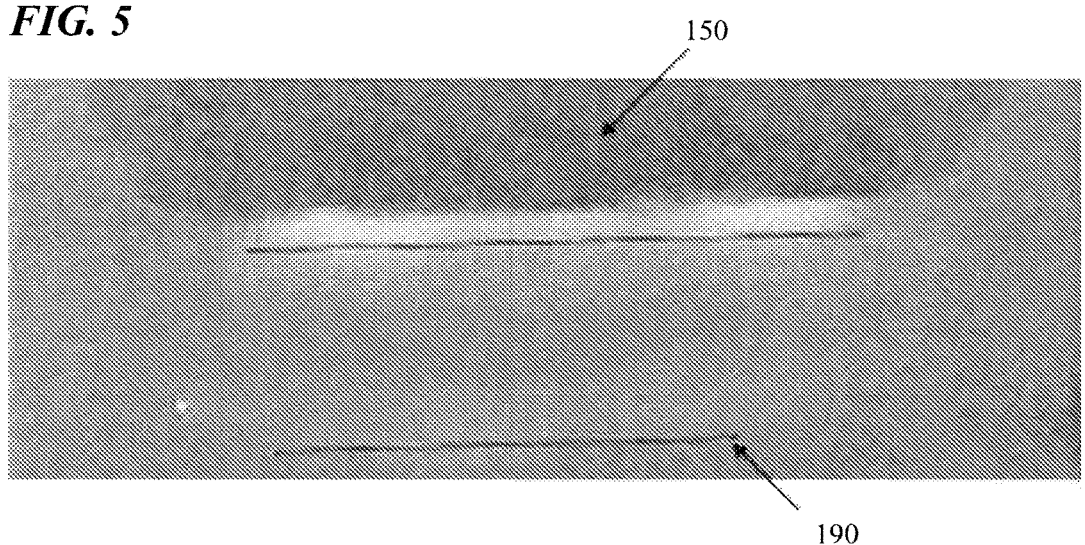
FIG. 5 illustrates further detail of thermal treatment for a shallow probe RF system with little cooling in the epidermal region and shows a zone of significant heating of fat/muscle interface.
Figure 6A:
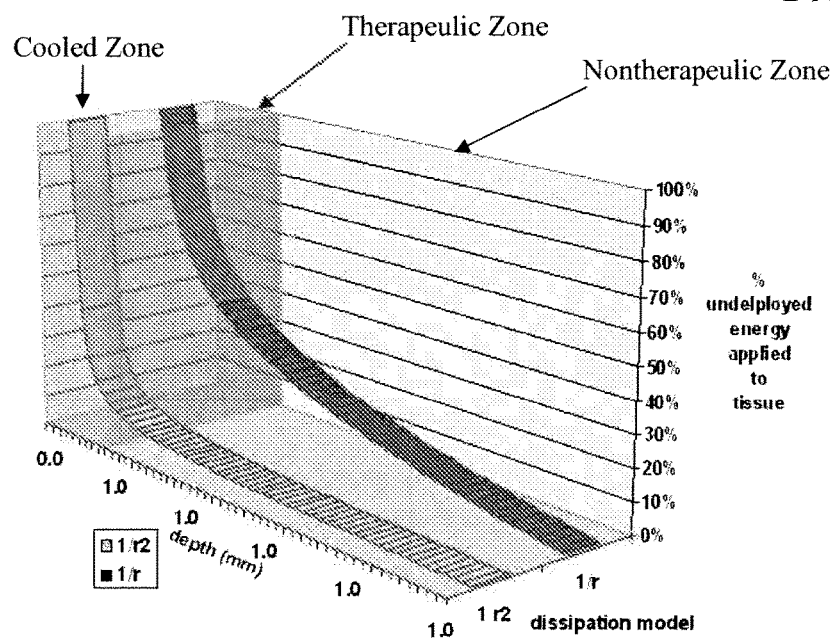
FIG. 6A illustrates a heat dissipation in a monopolar RF approach and FIG. 6B for a bipolar RF approach.
Figure 6B:
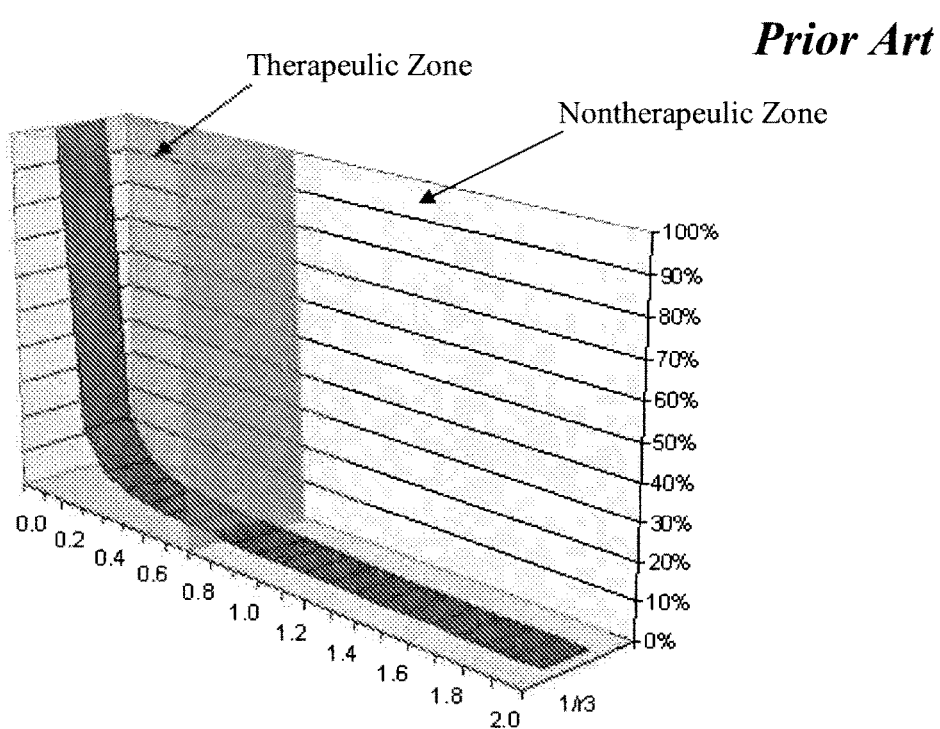
Figure 9A:
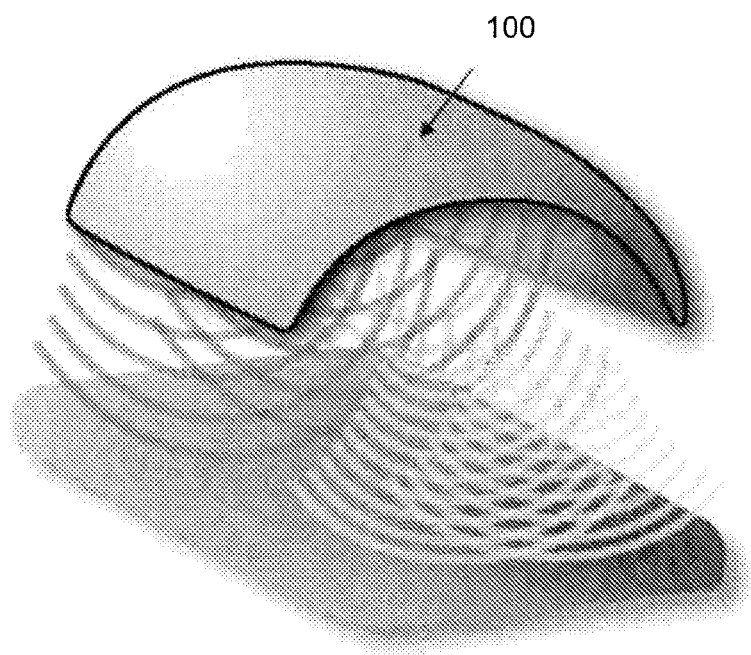
FIG. 9A shows a single transducer applying ultrasound to a specimen.
Figure 9B:
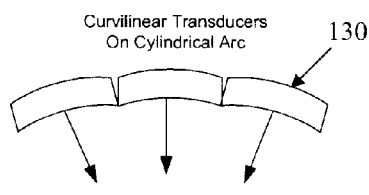
FIG. 9B shows an array of curvilinear transducers on a cylindrical arc.
Figure 9C:
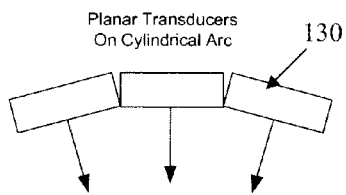
FIG. 9C shows planar transducers in an array and on a cylindrical arc.
Figure 9D:
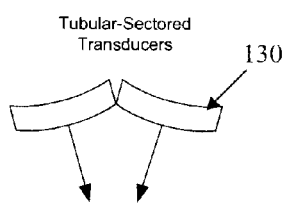
FIG. 9D shows tubular sectored transducers in an array along a curved arc.

As an example of preferred embodiments there are shown in FIGS. 9B-9D three configurations of the transducer arrays 130 that are based upon creating a sub-cylindrical longitudinal sectioning of a cylindrical transducer or alternatively, a parabolic-shaped transducer shape which we have used for creating "soft-focused" volumetric therapy zones in target tissue.

With regard to the zone of soft focus of acoustic energy which may be affected by the ultrasound delivery applicator device, that focus may be delivered by a single transducers 100 (see FIG. 9A), or a plurality of the transducer arrays 130 (see FIGS. 9B-9D) aligned adjacent to each other. In the case of each of the transducers 130, the exact size of the lateral pattern (size on skin surface) is determined by the transducer length along its long axis, its width (related to radius of curvature), frequency of operation, and desired zone of focus (depth and extent). Multiple areas and ones of the transducer arrays 130 can be assembled to form layer arrays (not shown). This permits larger areas to be covered with a single application. The arrays 130 may be configured from either planar rectilinear transducers, or from multiple smaller curvilinear transducers (see FIGS. 9B-9D). Additional configurations include cross-sections of the tubular form of the transducer arrays 130 with angular sectored regions. Further, these individual transducers 100 or the arrays 130 may be located within the applicator device to form a curvilinear region, permitting further concentration of energy in a narrower depth zone while having significant (2-4 cm) lateral coverage.

With the single transducer 100 of FIG. 9A, a pattern of thermal elevation (see FIG. 11) may be created which is as long as the curvilinear transducer (up to 9 cm in length for 3 transducers arranged longitudinally end-to-end) and from approximately 50% of the width of the transducer to 100%+ of the transducer width, depending upon transducer configuration.

Figure 11:
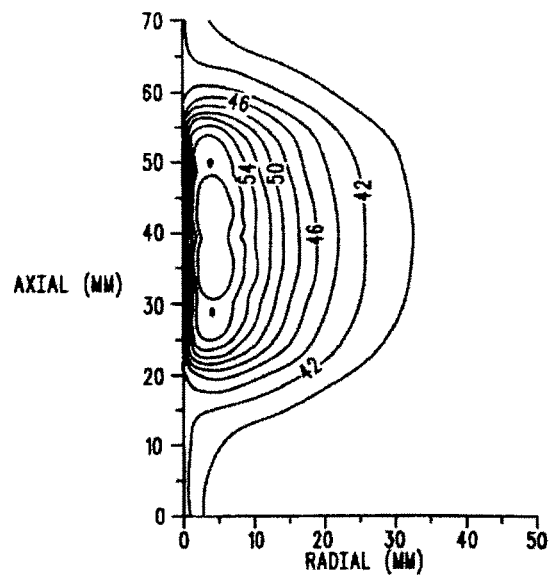
FIG. 11 shows a thermal profile created using the single transducer of FIG. 9A with isothermal temperatures in degrees Celsius.

The results of FIG. 11 were obtained with a 7 mm wide by 15 mm long (axial direction) single transducer 130. The emitting side of the transducer 100 is along the axial axis shown in FIG. 11 and emits energy in the positive radial direction. The temperature data in FIG. 11 were collected using very fine wire thermocouple linear arrays inserted parallel to the axial direction of the transducer. Because of mapping constraints, the last isotherm represented is 58° C. The central region of maximum focus is above 60° C. A 60° C. isotherm extends from approximately 3 mm deep (radially) with an axial length +/−5 mm on either side of 40 mm. The maximum temperature observed in the center of this zone was 66° C.

By adding more of the transducers 100 or the arrays 130, a plurality of the transducer 100, arrays 130 can be arranged to, simultaneously, heat more than one region along the length of, or across width of, the transducer array. As thermal diffusion occurs, the cross-section of the resultant zone of thermal dose becomes uniform in the region of energy deposition under the collective transducer array.

Figure 10:
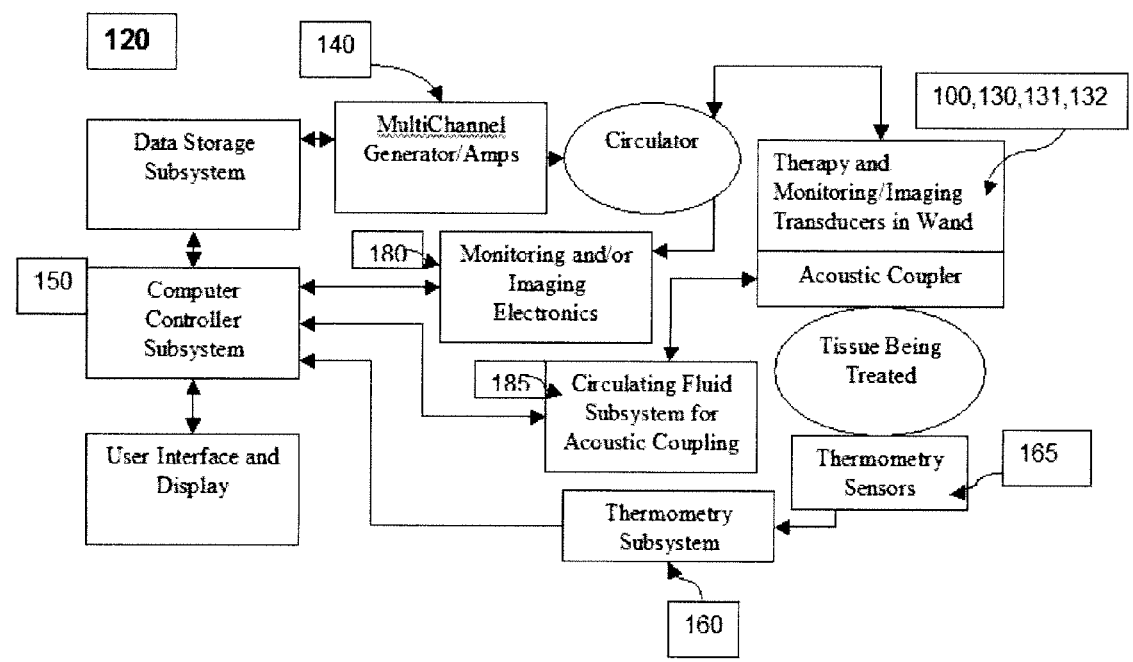
FIG. 10 is a block diagram of an ultrasound thermal therapy and monitoring system comprised of a computer controller, generator/amplifier subsystem, therapy/monitoring/imaging transducers, monitoring electronics, acoustic coupling and circulating fluid subsystem, and optional thermometry sensors and subsystem.

The ultrasound system 120, schematically depicted in FIG. 10, includes four primary components: the therapeutic transducer 100, arrays 130, RF generator 140, treatment control computer 150, and multi-channel thermometry system and data logger 160 with fine-wire thermocouple probes 165. The computer controller 145 controls the power level and drive frequency to the transducer 100 or the arrays 130. Additionally, the computer controller 145 can process information from the data logger 160, recording the temperature as a function of time just prior to, during, and immediately following the power-on period. A total of thirty-two channels are supported by the system 120.

In order to better understand the scope of the method and system of the invention, it is helpful to understand skin makeup, particularly collagen. Collagen is a molecule that configures itself as a helix. Cross-bonding of one collagen helix to another, or one portion of the helix within a collagen molecule to another portion of the helix in that same molecule, produces a system of molecules that can be likened to individual fibers in cloth, yarn, or puff (such as a cotton ball). The combination of helical strands and cross-linking provides both strength and flexibility to the tissue. Applying thermal energy to that collagen causes some of the cross-linking bonds to break. This allows the helical coil to tighten and, if the other components of the tissue structure are compressible, decreases the volume and increases the density of the structure. When the collagen cools, cross-linking bonds reform and the tighter, denser, structure is locked into place. As long as there are no excess sources of pressure (uncompressible tissue, exercise exertion) the cross-linking continues with time, making the more compact structure more permanent. Studies have shown that thermal remodeling of collagenous tissue can cause an increase in density of 20% to 50%. Additionally, the damage inflicted on the tissue stimulates the generation of more collagen, or neocollagenesis. As this neocollagenesis occurs, it causes the tissue to fill in with more connective tissue—strengthening and firming it, restoring many of the features which degrade with aging.

Collagen makes up 75% of the dry weight of skin. Most of that collagen is concentrated in the dermis, the layer of tissue underlying the epidermis (the outer layer of tissue, visible intact skin). The therapy mechanism is to heat the collagen in the dermis to a level where it will remodel, shrink, and stimulate neocollagenesis.

Among the means of collagen remodeling in the skin that are currently employed are chemical agents, light energy (including laser), (RF) or other forms of energy applied with the purpose of raising the temperature of the collagen in the dermis. The graph below, derived from investigations performed by Wall, et al., shows that collagen shrinkage is a function of time and temperature. Although shrinkage may occur at lower temperatures, the commercially viable ranges of time/temperature application are 60oC+ for approximately one second.

The degree to which the collagen is reduced in size by heating also affects the strength of the resulting tissue structure, and that may have a significant impact on the effectiveness and consistency of the treatment procedure. Wall's work also describes the tensile strength of shrunken collagen as a function of the amount of shrinkage. After the application of therapy that produces severe shrinkage, the resulting collagen structure is so weakened that, when equal opposing forces are applied, it will actually stretch to a greater overall length than if the tissue had not been shrunk in the first place. For example, when a stress of approximately 0.25 MPa is applied to a 10 cm bovine ligament which has been shrunk to 6 cm, the ligament will extend to 11 cm. The same stress applied to an untreated (that is, unshrunk) 10 cm bovine ligament tissue demonstrates negligible deformation.

If the collagen is shrunk less than 20% to 25% it remains stronger than untreated collagen, and for much higher stresses. Most thermal remodeling procedures do not control the heat applied to the tissue and have a goal of inducing maximum collagen shrinkage. The implications of this research are that collagen remodeling procedures are more likely to produce weakened tissue which will revert to the original condition—or worse—with stresses. Certain embodiments of the invention include the ability to image collagen density, and measure changes in collagen density, in real time. This feature will allow the clinician to affect optimal treatment in an image-guided procedure. An interesting byproduct of the shrinkage of collagen is that it results in an increase in the density of the tissue. That increased density associated with thermal remodeling of the collagen means that the acoustic density (thus, the ultrasound image) also changes. It has been demonstrated in the prior art that a 1.5% increase in the acoustic velocity with a 5% increase in collagen density. A similar correlation was demonstrated in the attenuation coefficient. These two properties allow for a direct ultrasound measurement of the change in tissue density as a function of collagen content.

A 30% shrinkage in collagen would result in a 40% increase in the density of the collagen molecules in the skin tissue. That change in tissue density would result in a change in acoustic velocity of almost 10%. This change will be visible to the ultrasound transducer that is affecting the change.

In the skin treatment application, collagen changes could result in 30% attenuation and 10% acoustic velocity changes. The embodiments of the invention can apply this in cross-correlation algorithms to monitor the treatment in real time using the same transducers as are used for therapy. Additionally, the tissue may be imaged and structural changes correlated with the resulting cross-correlated acoustic property changes.

Further, the methodology allows one to map density changes, enhancing the density changes with color coding. The ultrasound technology may be modified to image as well as treat. This feature makes it easier for the physician to distinguish temperature profiles and collagen changes—and more precisely control the procedure.

In one embodiment, the system can map the ecogenecity of the ultrasound image, correlating differences in reflectivity intensity (whiteness) with tissue density and structural changes, which present themselves as pattern changes in the B-mode images. The system automatically converts varying degrees of whiteness into a color map, making it easier for less sophisticated users to employ the technology.

In some applications this technology can be used to measure changes in tissue temperatures noninvasively. However, it is not necessary to monitor the temperature. Temperature monitoring is a predictive indicator of collagen shrinkage. In one embodiment, the collagen shrinkage is directly measured by measuring structural changes which are thermally-induced—the very effect that the treatment energy is attempting to achieve.

Over-application of thermotherapy is a problem encountered by the technologies in use today. In radiofrequency dermoplasty the control mechanisms are primarily application time and patient comfort level (i.e. pain). Uncontrolled temperature application can cause too much shrinkage in localized areas—resulting in dents and pits in the patient's face—or it can cause fat liquification of the underlying tissue.

The embodiment of the invention can measure the zone at which the application should be applied and measure collagen density in that region. Thus, when it heats the tissue, it can maintain a uniform application and monitor collagen density. Areas that are treated more than others would show up whiter. Thus, small amounts of energy can be applied—making certain that the ecogenicity of the underlying tissue stays constant—and an optimal treatment result will occur.

Another advantage to using ultrasound feedback to determine when thermal remodeling has occurred is that it allows more effective use of anesthetic to increase procedural comfort. Collagen bond de-linking typically occurs at 60° C. to 90° C. These temperatures can cause patient discomfort. RF methods of applying heat, however, are not precise. These limitations are due to fundamental limitations of the modality. They can often raise the temperature to the top end of this range—or higher—particularly near the surface or at dielectric boundaries. They depend on patient feedback (that is—pain) to determine when excess energy is being applied/absorbed and sensed by nerve receptors. Because of this factor, these approaches discourage the use of complete anesthetic block to remove pain. In certain applications of the invention, a user should be able to use a more complete anesthetic protocol—localized to the treatment site—during the procedure. The result will be a greatly enhanced comfort level during the procedure and a probable reduction of the need to use higher levels of sedation (Valium, Versed, etc.) to help the patient to cope with the procedure.

Using application time as a feedback mechanism is ineffective because small variations in temperature coupled with treatment duration can also affect the degree of collagen shrinkage and remodeling. For instance, a one second application of 70° C. heat causes 20% collagen shrinkage, while the same duration at 73° C. causes a 30% shrinkage.

By monitoring temperature—or the effect of temperature—during the procedure, the instant embodiments of the invention can maintain the temperature at the lower end of the range and, by greatly reducing the probability of raising the temperature and duration to the range of permanent physical damage, a more aggressive (and more comfortable) anesthetic protocol may be used.

The following nonlimiting examples illustrate use of the invention.

EXAMPLE 1

Skin tissue samples were mounted on a 2.5 cm thick hard rubber base and backed by acoustic absorber material. The samples were anchored using push pins. Two curvilinear transducers were used for the experimental studies. Both transducers were 0.8 cm width and 2.1 cm in length. The center frequency of the transducers were 7.7 MHz and 8.2 MHz, respectively. The radii of curvature were similar, being 3.6 mm for the 7.7 MHz transducer and 4.0 mm for the 8.2 MHz transducer. During the tests, 2.5 Watts were applied to the 3.6 mm dia (7.7 MHz) transducer and 12 Watts for the 4.0 mm dia (8.2 MHz) transducer.

Figure 12:
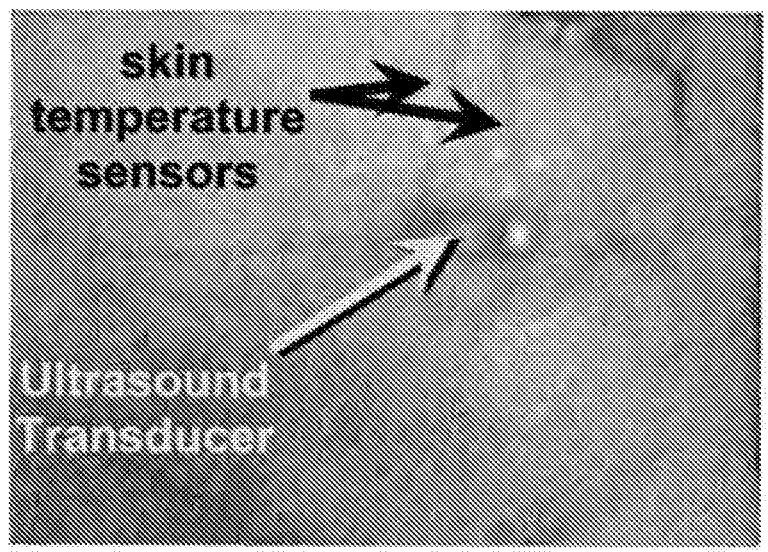
FIG. 12 shows a photograph of a single ultrasound transducer over the surface of a porcine skin sample with skin temperature sensors identified.
Figure 13A:
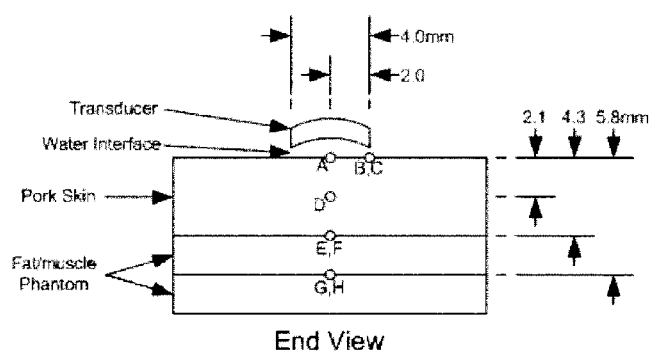
FIG. 13A shows an end view of experimental setup 1 for the Example 1 and FIGS. 13B and C show top and side views thereof.
Figure 13B:
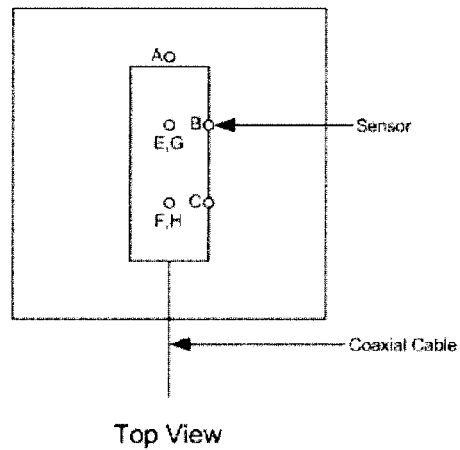
Figure 13C:
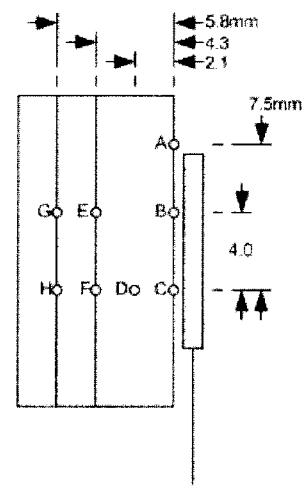
Figure 14A:
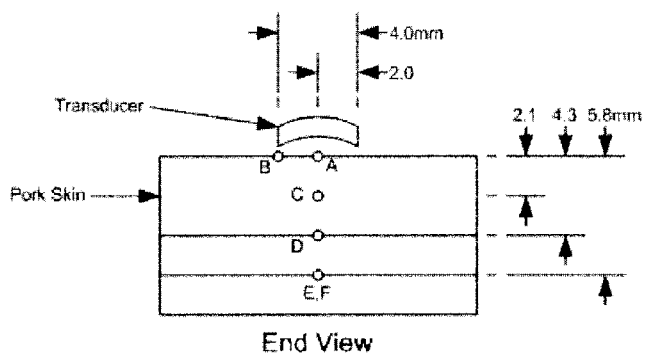
FIG. 14A shows an end view of experimental setup 2 of the Example 1 and FIGS. 14B and C show top and side views thereof.
Figure 14B:
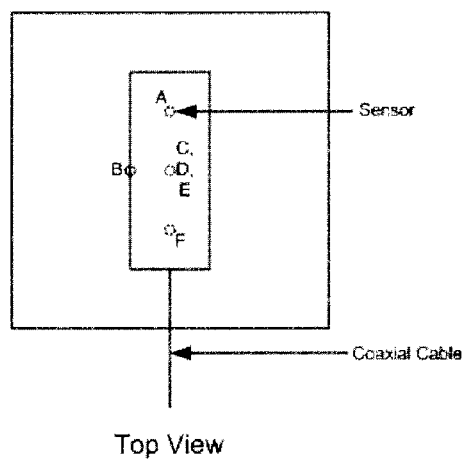
Figure 14C:
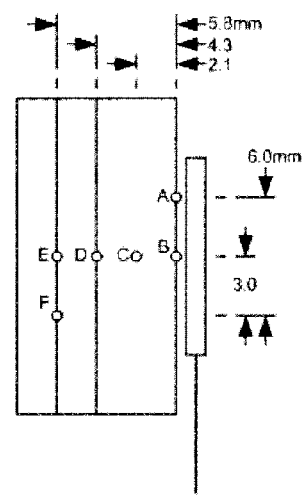

Temperature sensors were placed at the surface of the skin tissue, at a depth of 2.1 mm, 4.3 mm, and 5.8 mm beneath the skin surface. A photo of the setup on an ex-vivo skin tissue sample is shown in FIG. 12. Schematic diagrams of the setup configurations used for dosimetry studies for single curvilinear transducer are shown in FIGS. 13A-13C, Setup 1 and FIGS. 14A-14C for Setup 2. Other than the skin sensors, there was some margin of error in placement of the temperature sensors, estimated at +/−0.5 mm laterally and +/−0.25 mm in depth).

No surface flow cooling techniques were employed. There was a thin (~2 mm) layer of coupling liquid maintained at 30° C. between the ultrasound transducer and the skin, but the fluid was not circulated through a cooling device or chilled reservoir.

The results of the experimental studies in porcine skin tissue are described for the two setups in three skin tissue samples (Examples 2-4). Two transducers at center operating frequencies of 7.7 MHz and 8.2 MHz having slightly different radii of curvature were used for these experiments. No custom mounting handpiece was used to hold the transducers. They were positioned using a custom positioning device available in our laboratory.

EXAMPLE 2

Figure 15:
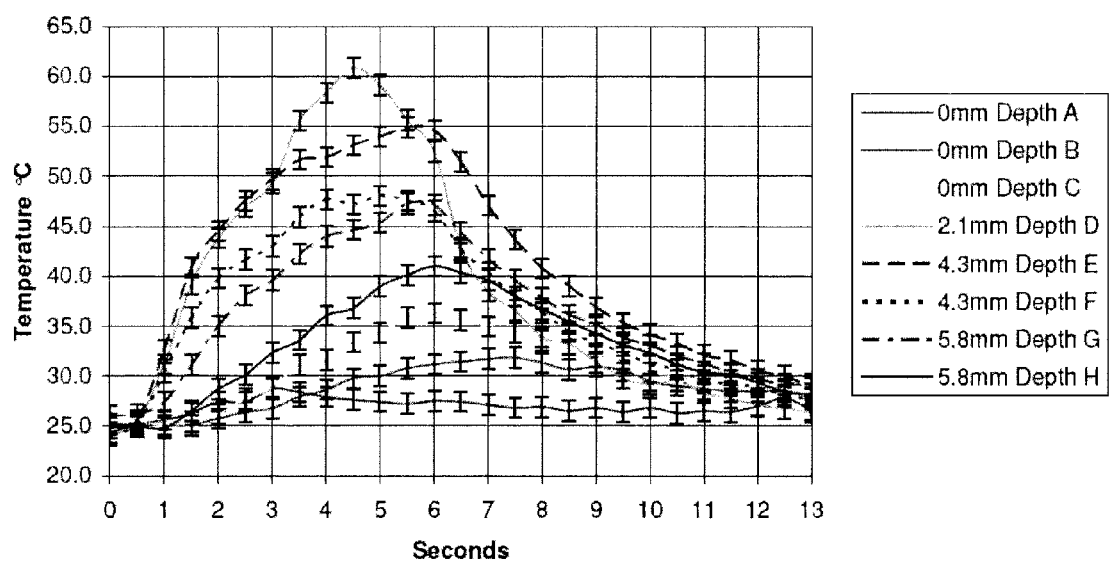
FIG. 15 shows the heating patterns as a function of time at different depths for Example 2 in porcine skin from 4.5 seconds of 12 watts of acoustic power at 8.2 MHz.
Figure 16:
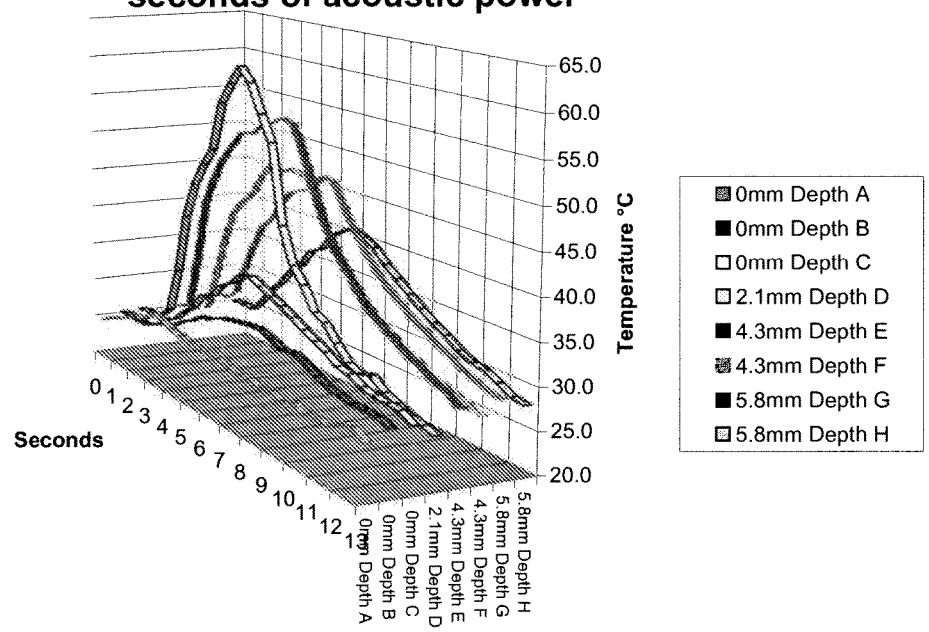
FIG. 16 shows the temperature heating pattern in three dimensions as a function of depth and time for individual sensors in skin tissue sample 1 for Example 2 located as in legend and insonated with 12 watts power at 8.2 MHz for 4.5 seconds.
Figure 17:
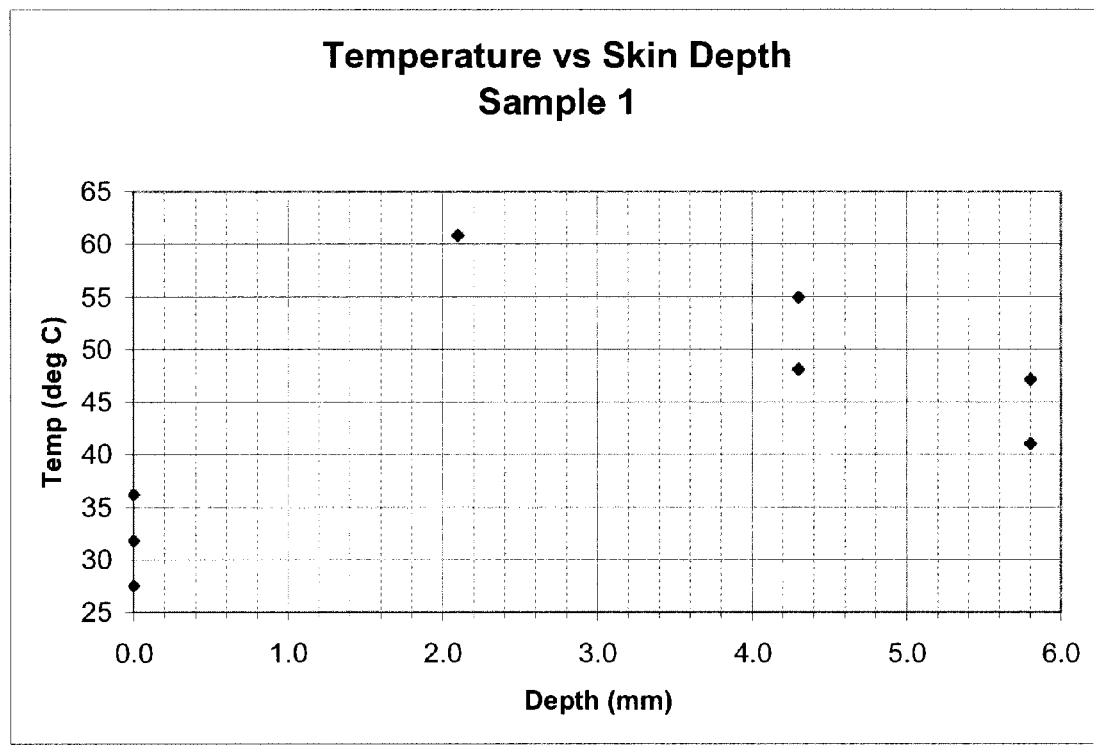
FIG. 17 shows temperature versus skin depth for sample 1 at time 4.5 seconds for individual sensors located as denoted and insonated with 12 watts acoustic power at 8.2 MHz.

In Sample 1, 12 Watts of acoustic power was applied at 8.2 MHz. As shown in FIG. 15, The maximum temperature was measured at the 2.1 mm deep thermocouple as expected for this transducer. In this test, the maximum temperature at 2.1 mm was measured at 61° C. at 4.5 sec, after which power was discontinued to the ultrasound transducer. The three surface thermocouples (A,B,C) measured 27° C., 29° C., and 33° C. respectively at 4.5 sec, but continued to rise to 27° C., 32° C., and 36° C. at times between 6 sec and 7 sec because of thermal conduction in the tissue and non-circulating cooling liquid (see FIG. 16). The 4.3 mm deep thermocouples (E,F) measured 53° C. and 47° C. at 4.5 sec, but sensor E continued to rise to 55° C., peaking at 5.8 sec (see FIG. 17). The 5.8 mm deep thermocouples (G,H) measured 44° C. and 36° C. respectively at 4.5 sec, but continued to rise to 41° C. and 47° C. at 6 sec due to thermal conduction.

EXAMPLE 3

Figure 18:
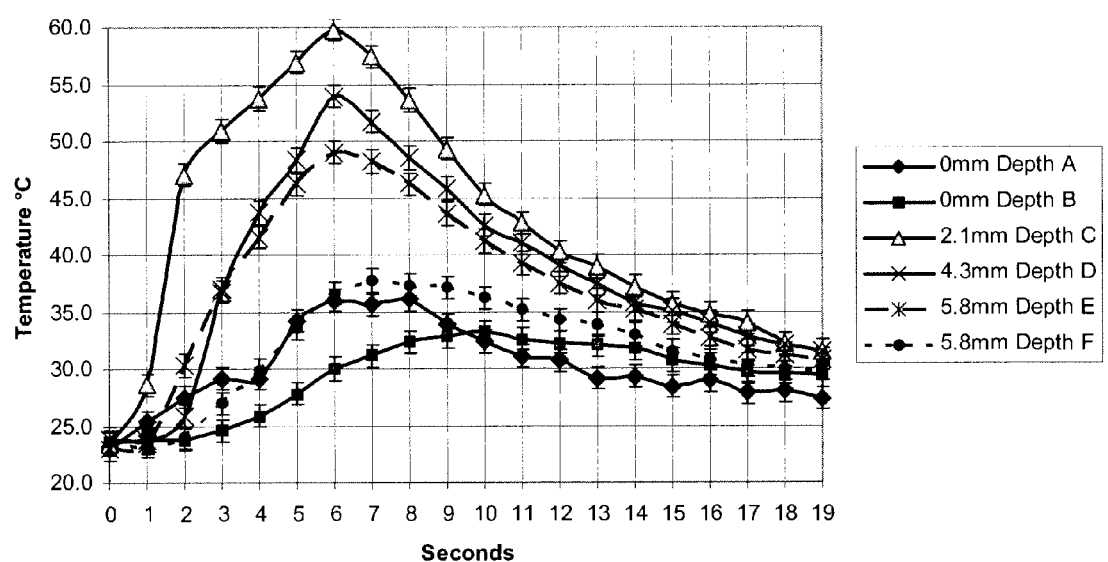
FIG. 18 shows the heating patterns as a function of time at various depths for Example 3 in porcine skin heated for 6 seconds with 8 watts of acoustic power at 8.2 MHz.
Figure 19:
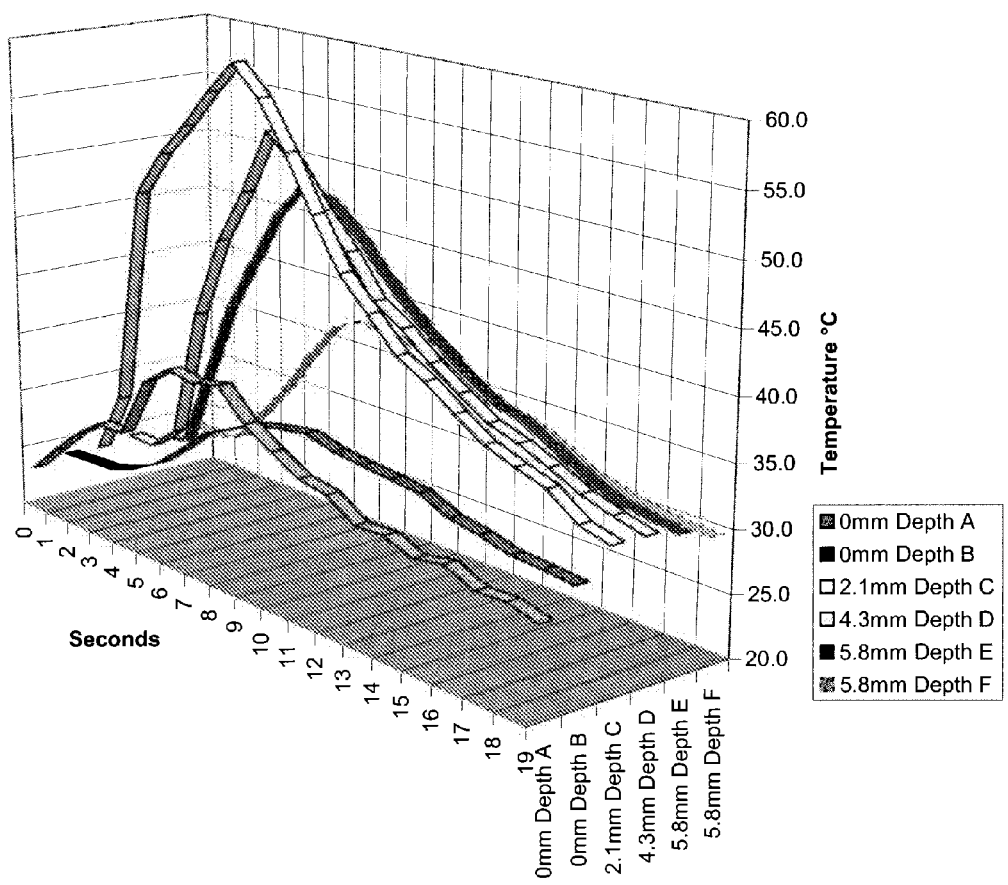
FIG. 19 shows the temperature heating power pattern for three dimensions as a function of depth for individual sensors in skin tissue sample 1 for Example 3 located as in the legend and insonated with 8 watts power at 8.2 MHz for 6 seconds.
Figure 20:
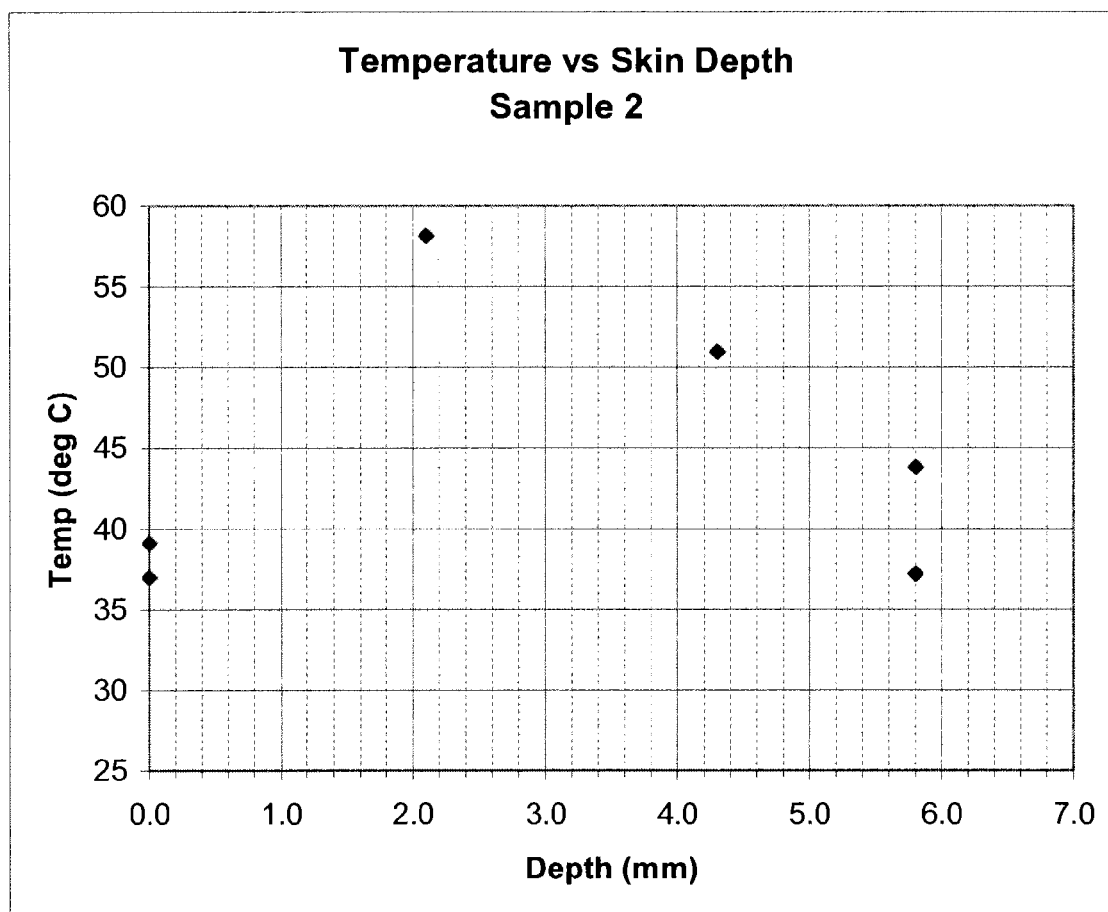
FIG. 20 shows temperature versus skin depth for Example 3 at time 6 seconds for individual sensors located as denoted and insonated with 8 watts acoustic power at 8.2 MHz.

In Sample 2, 8 Watts of acoustic power was applied at 8.2 MHz. As shown in FIG. 18 maximum temperature was measured at the 2.1 mm deep thermocouple as expected for this transducer. As illustrated in FIG. 19 this test, the temperature at 2.1 mm was measured at 60° C. at 6 sec, after which power was discontinued to the ultrasound transducer. The two surface thermocouples measured 30° C. and 36° C. at 6 sec but continued to rise to 36° C. and 33° C. at times between 6 sec and 10 sec because of thermal conduction in the tissue (see FIG. 20). The 2.1 mm deep thermocouple measured 54° C. at 6 sec. The 5.8 mm deep thermocouples measured 49° C. at 6 sec.

EXAMPLE 4

Figure 21:
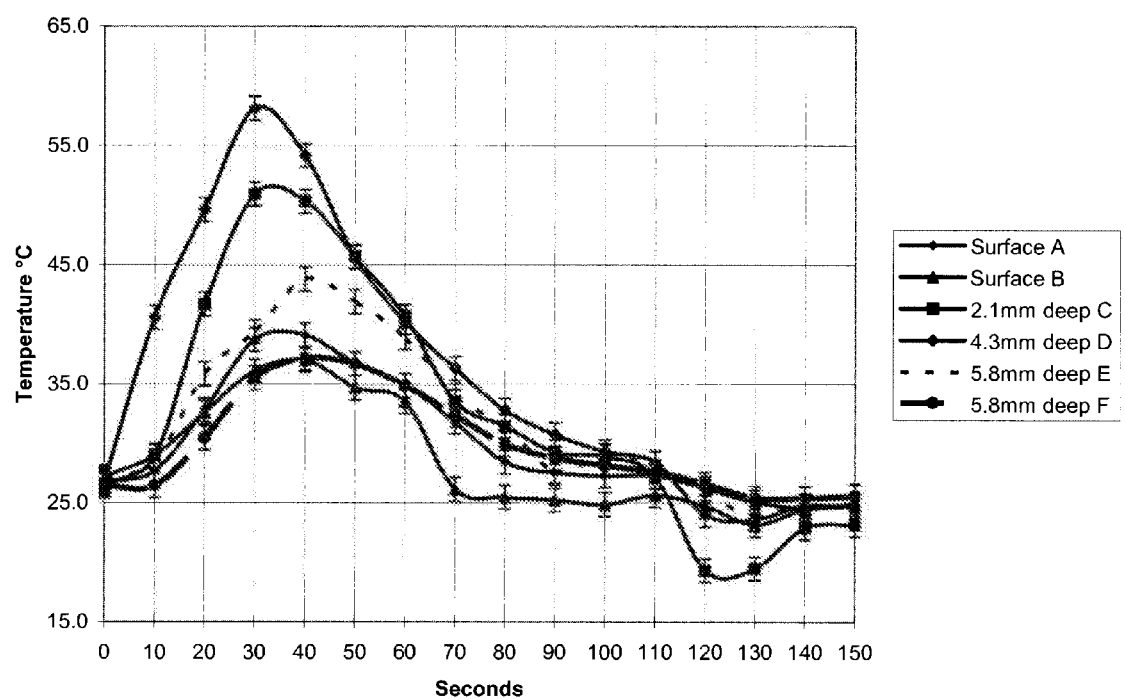
FIG. 21 shows the heating patterns as a function of time at various depths for Example 4 in porcine skin for 30 seconds at 2.5 watts of acoustic power at 7.7 MHz.
Figure 22:
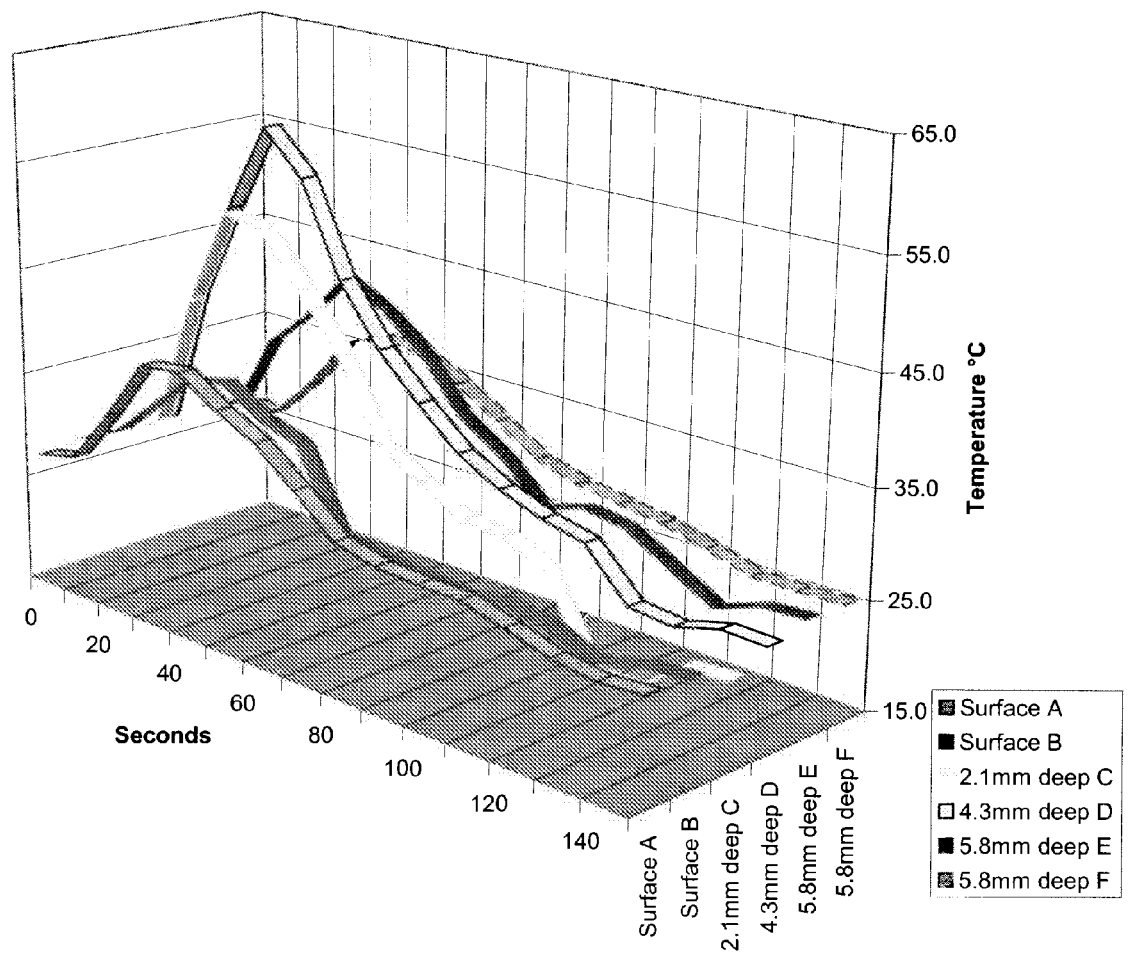
FIG. 22 shows the temperature heating power pattern for three dimensions as a function of depth for individual sensors in skin tissue sample 1 for Example 4 located as in legend and insonated with 2.5 watts power at 7.7 MHz for 30 seconds.
Figure 23:
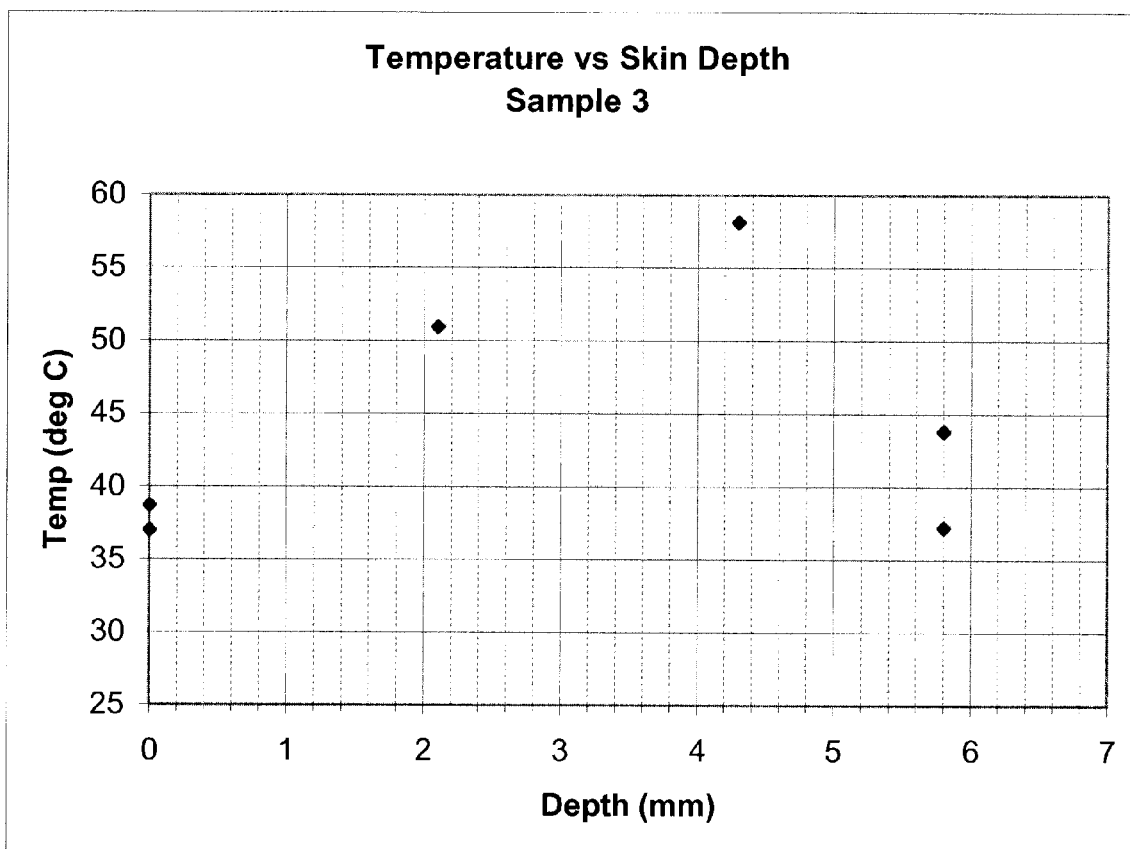
FIG. 23 shows temperature versus skin depth for Example 4 at time 30 seconds for individual sensors located as denoted and insonated with 2.5 watts acoustic power at 7.7 MHz.

In Sample 3, −2.5 Watts of acoustic power was applied at 7.7 MHz. The objective was to examine the time required for very low power application to achieve a therapeutic temperature of approximately 60° C. As shown in FIG. 21 the maximum temperature was measured at the 4.3 mm deep thermocouples, as expected for the 7.7 MHz transducer (see FIG. 22). In this test, the temperature at 4.3 mm was measured at 57° C. at 30 sec, after which power was discontinued to the ultrasound transducer. The two surface thermocouples measured 35° C. and 37° C. at 30 sec but continued to rise slightly to 36° C. and 38° C. respectively (at between 30 sec and 40 sec) because of thermal conduction, followed by temperature decay. As shown in FIG. 23 the 2.1 mm deep thermocouple measured 54° C. at 30 sec. The 5.8 mm thermocouples measured 30° C. and 39° C. at 30 sec and continued to rise to 37° C. and 44° C. during the following 10 sec because of thermal conduction in the tissue.

In these examples the objective was to achieve a therapeutic temperature of 60° C. or greater. In studies 1 and 2, a local temperature maximum was achieved within a few seconds while the surface tissue and deeper tissue elevations were minimal. The targeted zones (2 mm to 4 mm deep) achieved the desired temperature increase of 60° C. in two of the three studies. In addition, these temperatures were achieved in less than 6 seconds. In the third study, a different transducer operating at a center frequency of 7.7 MHz and only 2.5 watts acoustic power was used and the insonation time to reach therapeutic temperature increased significantly (30 sec). This was performed to examine the effects of thermal conduction in skin tissue. Although some conduction effect was noted, particularly at the deep sensor positions, it was small considering that these studies were performed using ex-vivo tissues.

The temperature profiles achieved local maximums at different times. This is due to the different insonation power levels employed for each study. The temperature in the region where the local maximum occurred declined immediately upon cessation of power. Those temperature sensors closest to the depth where local maximum occurred achieved maximum at slightly longer times post cessation of power application. The time to achieve the maximum was related to the distance of the temperature sensor from the maximum temperature location. This behavior is consistent with conductive heat dissipation, which is expected in ex-vivo tissue samples. Had active flowing surface cooling techniques been applied during the studies, the surface temperature sensors would have remained consistently lower immediately following application of power. The cooling employed in these studies was static 25-30° C. coupling fluid for insonation.

Figure 24A:
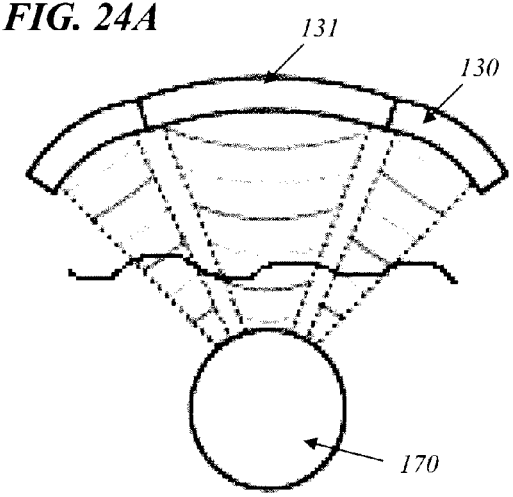
FIG. 24A shows an array of three curvilinear transducers of different sizes placed in an arc to focus energy to a tissue region beneath the surface of the skin.
Figure 24B:
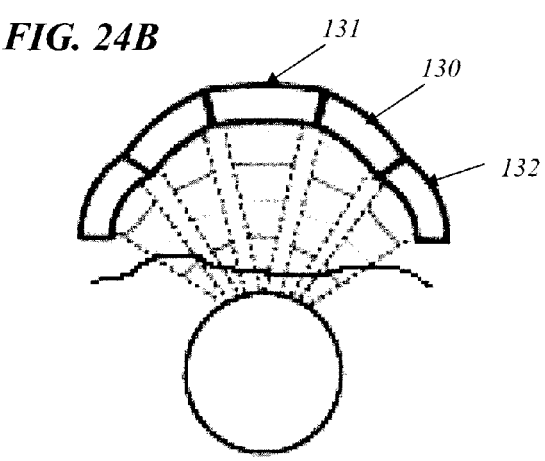
FIG. 24B shows an array of five curvilinear transducers of different curvatures placed in an arc and focused to a region beneath the skin.
Figure 24C:
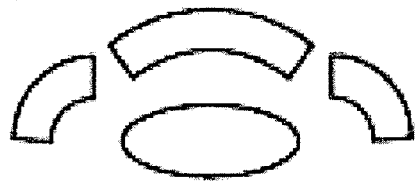
FIG. 24C shows an array of three transducers on an arc with different curvatures and spacing between the transducers.
Figure 25A:
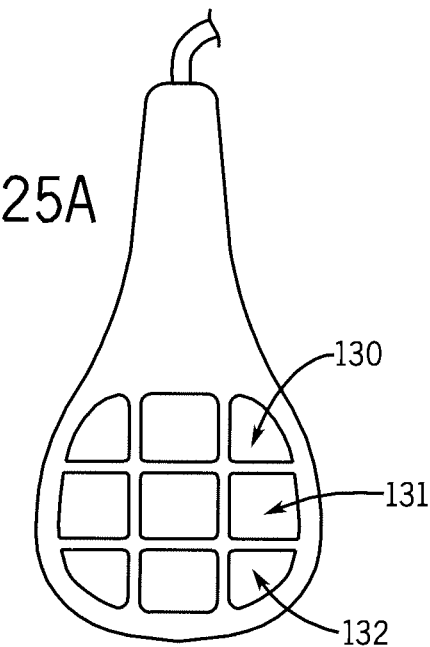
FIGS. 25A through 25D shows four different configurations of transducer arrays within treatment wands or handpieces for treating different sized regions of the skin.
Figure 25B:
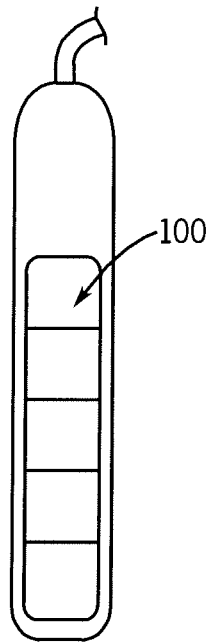
Figure 25C:
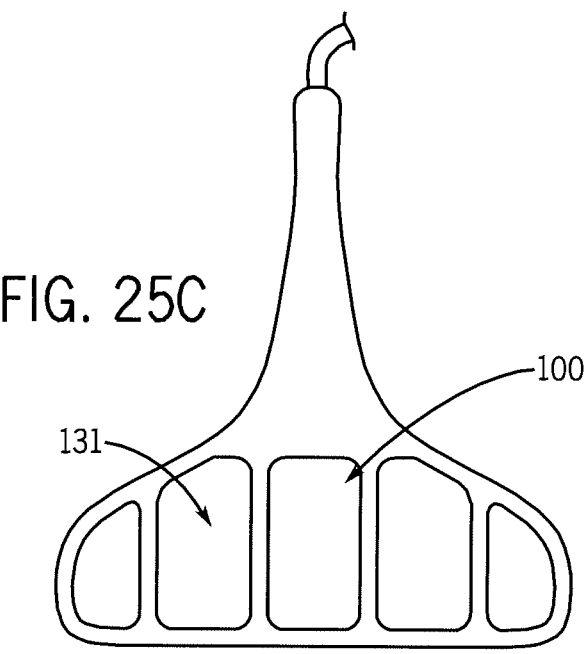
Figure 25D:
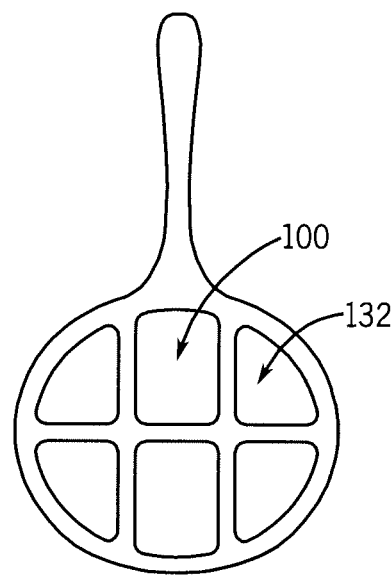

The transducer configuration of FIG. 24A includes transducers 130 and 131 of two different sizes which produce a composite focal zone 170 of a designed depth, size, and shape in accordance with specific design parameters of frequency, curvature, cross-sectional area, and array stacking. Similarly the five transducer configuration of FIG. 24B produces a designed energy focal region using transducers 130, 131, and 132 of different curvatures. All transducers in the array may operate at a single frequency, at different frequencies, or over a range of frequencies. In FIG. 24C, the transducers 131 and 132 are spaced on an arc and are of different curvatures.

Transducer arrays of different configurations are shown mounted inside handpieces in FIGS. 25A-25D. Transducers 100, 130, 131, 132 are configured on different arcs and with differing curvatures to produce treatment zones that are focused in the dermal and sub-dermal tissues layers or at greater depths corresponding to the fat muscle interface. The transducer curvatures, arc curvature, and frequency can be further configured to produce focal zones in even deeper tissue regions ranging from one to eight centimeters for the treatment of adipose tissues.

Figure 26A:
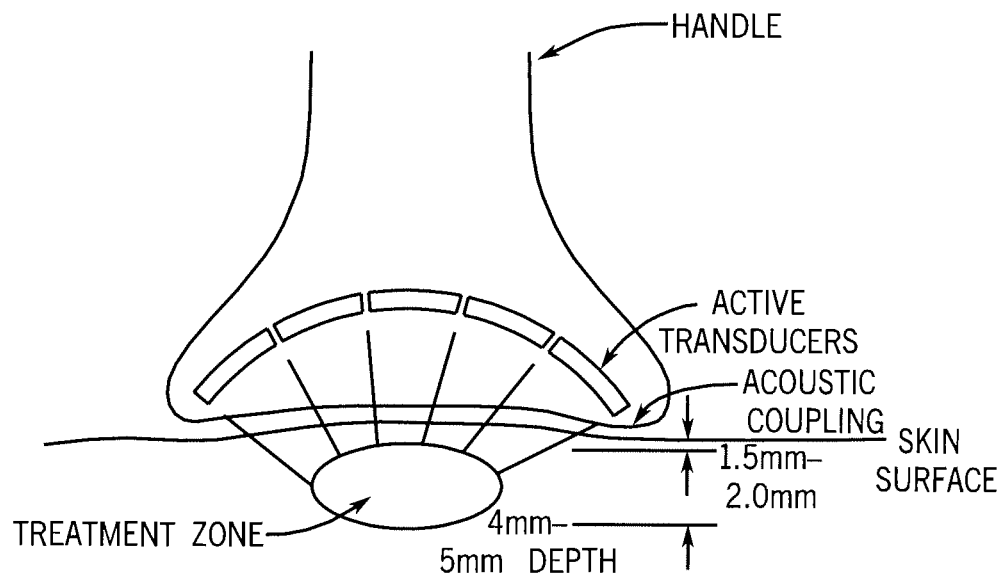
FIG. 26A shows a handpiece containing an array of transducers on a cylindrical arc and a fluid-filled acoustic coupling membrane in contact with the skin surface.
Figure 26B:
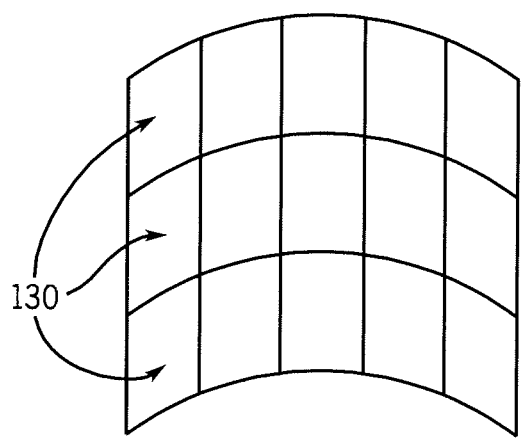
FIG. 26B shows one array configuration of three stacked five-element arrays that are contained within the handpiece.

FIGS. 26A and 26B show one embodiment of the invention mounted within a treatment handpiece or wand which includes an acoustic coupler. The acoustic coupler can be detachable or integral to the handpiece and could also be disposable. In one embodiment, the coupler would be filled either with degassed water or mineral oils or other fluids that minimally attenuate acoustic energy. The curvature of the arc and individual transducers are designed to produce a treatment zone at the desired target depth and with a lateral coverage area of the desired size. The arc arrays are stacked as in FIG. 26B if desirable for treating larger areas.

In FIG. 27A an end view of one embodiment of curvilinear transducers within a handpiece is shown coupled to the skin. A side view of one embodiment of the invention showing three curvilinear arrays end-to-end coupled to the skin is shown in FIG. 27B. The focal zones 175 are the desired treatment depth and area for the specific configuration based upon appropriate implementation of multiple design criteria which influence choice of frequency, curvature and other parameters.

It should be understood that various changes and modifications referred to in the embodiment described herein would be apparent to those skilled in the art. Such changes and modifications can be made without departing from the spirit and scope of the present invention.

What is claimed is:

1. A method of modifying collagen containing tissue at a treatment site to achieve a desired treatment, comprising steps of:
providing a plurality of sources of ultrasound energy outputting ultrasound energy beams to treat a specific region of interest and also causing formation of a reflected ultrasound image or ultrasound intensity, the plurality of sources comprising an arcuate ultrasound transducer configuration disposed on a common radius of curvature relative to the treatment site of the tissue, the arcuate ultrasound transducer configuration comprising a plurality of individual curvilinear ultrasound transducers arranged side to side on the common radius of curvature, each individual curvilinear ultrasound transducer having a radius of curvature and producing an individual focal zone of ultrasound energy;
directing a plurality of ultrasound energy beams from the arcuate ultrasound transducer configuration to the treatment site, wherein individual focal zones of the plurality of individual curvilinear ultrasound transducers combine to produce a rectangular combined focal zone that is not focused at a point, the combined focal zone having a length, a width and a depth;
controlling the ultrasound energy beams to intersect to establish a specific treatment volume in the tissue at the treatment site; and
controlling ultrasound energy input to the tissue based on the sensed reflected ultrasound image or ultrasound intensity by an ultrasound sensor wherein the sensed reflected ultrasound image or ultrasound intensity provides a real time indication of collagen density in the specific region of interest such that uniform application of the ultrasound energy beams is configured to be maintained, as indicated by a constant echogenicity from underlying tissues,
wherein the plurality of individual curvilinear ultrasound transducers comprise at least one ultrasound transducer operated at a different frequency than another ultrasound transducer, and
wherein the arcuate ultrasound transducer configuration consists of a plurality of different arcuate shapes.

2. The method as defined in claim 1, wherein the arcuate ultrasound transducer configuration has a non-linear cross section, and individual curvilinear ultrasound transducers in the arcuate ultrasound transducer configuration have a smaller radius of curvature relative to the common radius of curvature about the treatment site.

3. The method as defined in claim 2, wherein the non-linear cross section comprises at least one of a cylindrical cross section or a parabolic cross section.

4. The method as defined in claim 2, wherein the arcuate ultrasound transducer configuration comprises sections separated from each other, each section having a different radius of curvature.

5. The method as defined in claim 1, wherein the ultrasound sensor comprises at least one ultrasound transducer for sensing reflected ultrasound over the treatment site, thereby allowing control of ultrasound energy input to the tissue over the treatment site.

6. The method as defined in claim 1, wherein the arcuate ultrasound transducer configuration comprises at least one of a section of a cylindrical shape, a parabolic shaped transducer, a tubular form of transducer, or a sub-cylindrical longitudinal section of a cylindrical transducer wherein individual curvilinear ultrasound transducers have a smaller arc length relative to a common arc length about the treatment site.

7. The method as defined in claim 6, wherein the arcuate ultrasound transducer configuration is disposed at different angular orientations relative to a target axis, thereby enabling controlled thermal treatment over selected spatial locations.

8. The method as defined in claim 1, wherein the plurality of different arcuate shapes comprise a cylindrical shape and a parabolic shape.

9. The method as defined in claim 1, wherein the arcuate ultrasound transducer configuration comprises a plurality of individual curvilinear transducers disposed within an ultrasound applicator configuration.

10. The method as defined in claim 1, wherein selected individual curvilinear ultrasound transducers of the arcuate ultrasound transducer configuration have different focal depths, thereby enabling simultaneous controlled depth of ultrasound energy deposition into dermal/subdermal tissue.

11. The method as defined in claim 1, wherein selected individual curvilinear ultrasound transducers of the arcuate ultrasound transducer configuration have different focal volumes, thereby enabling controlled volume of ultrasound energy deposition into dermal/subdermal tissue.

12. The method as defined in claim 1, wherein the individual curvilinear ultrasound transducers further comprise at least one of transducers having different sizes, transducers having different curvatures, or a plurality of stacks of arranged transducers.

13. The method as defined in claim 1, wherein differences in reflectivity intensity that are indicative of collagen density are depicted in the sensed reflected ultrasound image as varying degrees of whiteness.

14. The method as defined in claim 1, wherein the arcuate ultrasound transducer configuration further comprises the plurality of individual curvilinear ultrasound transducers arranged end to end with the plurality of individual curvilinear ultrasound transducers that are arranged side to side on the common radius of curvature.

15. The method as defined in claim 1, wherein the plurality of sources of ultrasound energy comprise an array of arcuate ultrasound transducer configurations oriented such that individual curvilinear ultrasound transducers of one arcuate ultrasound transducer configuration are arranged end to end with individual curvilinear ultrasound transducers of another arcuate ultrasound transducer configuration.

16. A method of modifying collagen containing tissue at a treatment site to achieve a desired treatment, comprising steps of:
providing a plurality of sources of ultrasound energy outputting ultrasound energy beams to treat a specific region of interest and also causing formation of a reflected ultrasound image or ultrasound intensity, the plurality of sources comprising an arcuate ultrasound transducer configuration disposed on a common radius of curvature relative to the treatment site of the tissue, the arcuate ultrasound transducer configuration comprising a plurality of individual curvilinear ultrasound transducers arranged in rows and columns, individual curvilinear ultrasound transducers of each row being arranged side to side on the common radius of curvature, each individual curvilinear ultrasound transducer having a radius of curvature and producing an individual focal zone of ultrasound energy;
directing a plurality of ultrasound energy beams from the arcuate ultrasound transducer configuration to the treatment site, wherein individual focal zones of the plurality of individual curvilinear ultrasound transducers combine to produce a plurality of rectangular combined focal zones, each combined focal zone corresponding to a row of individual curvilinear ultrasound transducers, each of the combined focal zones having a length, a width and a depth;
controlling the ultrasound energy beams to intersect to establish a specific treatment volume in the tissue at the treatment site; and
controlling ultrasound energy input to the tissue based on the sensed reflected ultrasound image or ultrasound intensity by an ultrasound sensor wherein the sensed reflected ultrasound image or ultrasound intensity provides a real time indication of collagen density in the specific region of interest such that uniform application of the ultrasound energy beams is configured to be maintained, as indicated by a constant echogenicity from underlying tissues,
wherein the plurality of individual curvilinear ultrasound transducers comprise at least one ultrasound transducer operated at a different frequency than another ultrasound transducer, and
wherein the arcuate ultrasound transducer configuration consists of a plurality of different arcuate shapes.

17. The method as defined in claim 1, wherein
the plurality of individual curvilinear ultrasound transducers are arranged in rows and columns, the individual curvilinear ultrasound transducers of each row being arranged side to side on the common radius of curvature,
individual focal zones of the plurality of individual curvilinear ultrasound transducers combine to produce a plurality of combined focal zones, each combined focal zone corresponding to a row of individual curvilinear ultrasound transducers, and
the plurality of combined focal zones are spaced along a length of the arcuate ultrasound transducer configuration at a distance equal to a distance between rows of individual curvilinear ultrasound transducers.

18. The method as defined in claim 1, wherein directing the plurality of ultrasound energy beams from the arcuate ultrasound transducer configuration to the treatment site comprises contacting an external surface of skin above the treatment site with an external applicator containing the arcuate ultrasound transducer configuration.

19. The method as defined in claim 1, wherein
the arcuate ultrasound transducer configuration is not flexible, and
controlling the ultrasound energy beams to intersect to establish the specific treatment volume in the tissue at the treatment site comprises varying at least one of
a size of at least one of the plurality of individual curvilinear ultrasound transducers,
a spacing between at least one adjacent pair of individual curvilinear ultrasound transducers,
a degree of curvature of the radius of curvature of at least one of the individual curvilinear ultrasound transducers, or
a degree of curvature of the common radius of curvature.

20. The method as defined in claim 16, wherein the plurality of rectangular combined focal zones are spaced along a length of the arcuate ultrasound transducer configuration at a distance equal to a distance between rows of individual curvilinear ultrasound transducers.

21. The method as defined in claim 1, wherein the at least one ultrasound transducer and the another ultrasound transducer are operated at different frequencies via a control computer.

* * * * *